US006140471A

United States Patent [19]
Johnson et al.

[11] Patent Number: 6,140,471
[45] Date of Patent: Oct. 31, 2000

[54] METHODS FOR PRODUCING MEMBERS OF SPECIFIC BINDING PAIRS

[75] Inventors: Kevin Stuart Johnson; Gregory Paul Winter; Andrew David Griffiths; Andrew John Hammond Smith, all of Cambridge, United Kingdom; Peter Michael Waterhouse, Canberra, Australia

[73] Assignees: Cambridge Antibody Technology, Ltd., Cambridgeshire; Medical Research Council, London, both of United Kingdom

[21] Appl. No.: 09/050,783

[22] Filed: Mar. 30, 1998

Related U.S. Application Data

[63] Continuation of application No. 08/307,619, filed as application No. PCT/GB93/00605, Mar. 24, 1993.

[30]     Foreign Application Priority Data

Mar. 24, 1992 [GB] United Kingdom .................... 9206318

[51] Int. Cl.⁷ ...................................................... C12P 21/08
[52] U.S. Cl. ........................................................ 530/387.3
[58] Field of Search ............................... 530/387.1, 387.3

[56]                    References Cited

U.S. PATENT DOCUMENTS

| | | |
|---|---|---|
| 4,190,495 | 2/1980 | Curtiss, III . |
| 4,816,397 | 3/1989 | Bass et al. . |
| 4,946,778 | 8/1990 | Ladner et al. . |
| 5,223,409 | 6/1993 | Ladner et al. . |
| 5,733,743 | 3/1998 | Johnson et al. . |

FOREIGN PATENT DOCUMENTS

| | | |
|---|---|---|
| 27617/88 | 7/1989 | Australia . |
| 0 324 162 A1 | 12/1988 | European Pat. Off. . |
| WO 88/06630 | 9/1988 | WIPO . |
| WO 88/09344 | 12/1988 | WIPO . |
| WO 90/02809 | 3/1990 | WIPO . |
| WO 90/05144 | 5/1990 | WIPO . |
| WO 90/14424 | 11/1990 | WIPO . |
| WO 90/14430 | 11/1990 | WIPO . |
| WO 90/14443 | 11/1990 | WIPO . |
| WO 91/02801 | 3/1991 | WIPO . |
| WO 91/10737 | 7/1991 | WIPO . |
| WO 91/17271 | 11/1991 | WIPO . |
| WO 92/01047 | 1/1992 | WIPO . |
| WO 92/06204 | 4/1992 | WIPO . |
| WO 92/09690 | 6/1992 | WIPO . |
| WO 92/18619 | 10/1992 | WIPO . |
| WO 92/20791 | 11/1992 | WIPO . |
| WO 93/11236 | 6/1993 | WIPO . |
| WO 93/19172 | 9/1993 | WIPO . |
| WO 94/14424 | 7/1994 | WIPO . |
| WO 94/14443 | 7/1994 | WIPO . |

OTHER PUBLICATIONS

Abremski, K. et al., "Studies on the Properties of P1 Site–Specific Recombination: Evidence for Topologically Unlinked Products following Recombination," *Cell,* 32:1301–1311 (Apr. 1983).

Armstrong, J. et al., "Domain Structure of Bacteriophage fd Adsorption Protein," *FEBS Letters,* 135(1):167–172 (1981).

Bass, S. et al., "Hormone Phage: An Enrichment Method for Variant Proteins with Altered Binding Properties," *Proteins,* 8(4):309–314 (1990).

Better, M. et al., "*Escherichia coli* Secretion of an Active Chimeric Antibody Fragment," *Science,* 240:1041–1043 (1988).

Bird, R. et al., "Single–Chain Antigen–Binding Proteins," *Science,* 242:423–426 (1988).

Boyd, A.C., "Turbo Cloning: A Fast, Efficient Method for Cloning PCR Products and Other Blunt–ended DNA Fragments into Plasmids," *Nucleic Acids Research,* 21(4):817–821 (1993).

Carter, P. et al., "Improved oligonucleotide site–directed mutagenesis using M13 vectors," *Nucleic Acids Research,* 13(12):4431–4443 (1985).

Casali, P. et al., "Human Monoclonals from Antigen–Specific Selection of B Lymphocytes and Transformation by EBV," *Science,* 234:476–479 (1986).

Cathala, G. et al., "Laboratory Methods A Method for Isolation of Intact, Translationally Active Ribonucleic Acid," *DNA,* 2(4):329–335 (1983).

Chiang, Y.L. et al., "Direct cDNA Cloning of the Rearranged Immunoglobulin Varialble Region," *BioTechniques,* 7(4):360–366 (1989).

Clackson, T. et al., "Making antibody fragments using phage display libraries," *Nature,* 352:624–628 (1991).

Clonetech, cDNA & Genomic Libraries, Clonetech Laboratories, Inc., Palo Alto, California, USA, pp. 75–96 and 192 (1995/1996).

Cregg, J.M. et al., "Short Communication: Use of Site–Specific Recombination to Regenerate Selectable Markers," *Molecular Gen. Genet.,* 219:320–323 (1989).

Dale, E.C. et al., "Gene Transfer with Subsequent Removal of the Selection Gene from the Host Genome," *Proc. Natl. Acad. Sci., USA,* 88:10558–10562 (Dec. 1991).

(List continued on next page.)

*Primary Examiner*—James Ketter
*Attorney, Agent, or Firm*—Marshall, O'Toole, Gerstein, Murray & Borun

[57]            ABSTRACT

Methods, recombinant host cells and kits are disclosed for the production of members of specific binding pairs (sbp), e.g. antibodies, using display on the surface of secreted replicable genetic display packages (rgdps), e.g. filamentous phage. To produce a library of great diversity, recombination occurs between first and second vectors comprising nucleic acid encoding first and second polypeptide chains of sbp members respectively, thereby producing recombinant vectors each encoding both a first and a second polypeptide chain component of an sbp member. The recombination may take place in vitro or intracellularly and may be site-specific, e.g. involving use of the loxP sequence and mutants thereof. Recombination may take place after prior screening or selecting for rgdps displaying sbp members which bind complementary sbp member of interest.

18 Claims, 8 Drawing Sheets

OTHER PUBLICATIONS

De la Cruz, V.F. et al., "Immunogenicity and Epitope Mapping of Foreign Sequences via Genetically Engineered Filamentous Phage," *J. Biological Chemistry*, 263(9):4318–4322 (Mar. 25, 1988).

Dower, W.J. et al., "High Efficiency Transformation of *E. coli* by High Voltage Electroporation," *Nucleic Acids Research*, 16(13):6127–6145 (1988).

Fuchs, P. et al., "Targeting Recombinant Antibodies to the Surface of *Escherichia coli*: Fusion to a Peptidoglycan Associated Lipoprotein," *BioTechnology*, 9:1369–1373 (1991).

Fukushige, S. et al., "Genomic Targeting with a Positive–selection lox Integration Vector Allows Highly Reproducible Gene Expression in Mammalian Cells," *Proc. Natl. Acad. Sci.*, 89:7905–7909 (1992).

Gage et al., "A Cell–Free Recombination System for Site–Specific Integration of Multigenic Shuttle Plasmids into the Herpes Simplex Type 1 Genome," *J. Virology*, 66(9):5509–5515 (Sep., 1992).

Gherardi, E. et al., "A single–step procedure for cloning and selection of antibody–secreting hybridomas," *J. Immunological Methods*, 126:61–68 (1990).

Grant, R.A. et al., "Structure of the Filamentous Bacteriophage fl," *J. Biological Chemistry*, 256(1):539–546 (1981).

Griffiths, A.D. et al., "Isolation of High Affinity Human Antibodies Directly from Large Synthetic Repertoires," *EMBO J.*, 13(14):3245–3260 (1994).

Griffths, G.M. et al., "Somatic mutation and the maturation of immune response to 2–phenyl oxazolone," *Nature*, 312:271–275 (1984).

Harlow, E. et al., in *Antibodies A Laboratory Manual*, Cold Spring Harbor Laboratory, Cold Spring Harbor, New York, pp. 174–195, 216 (1988).

Hoekstra et al., "A Tn3 Derivative That Can Be Used to Make Short In–Frame Insertions Within Genes," *Proc. Natl. Acad. Sci., USA*, 88:5457–5461 (Jun., 1991).

Hoess, R.H. et al., "The Cre–lox Recombination System," in *Nucleic Acids and Molecular Biology*, Eckstein et al., (eds.), vol. 4, Springer–Verlag, Berlin, Heidelberg, pp. 99–109 (1990).

Hoess, R.H. et al., "The Role of the loxP Spacer Region in P1 Site–specific Recombination," *Nucleic Acids Research*, 14(5):2287–2300 (1986).

Hoogenboom, H.R. et al., "Multi–subunit proteins on the surface of filamentous phage: methodologies for displaying antibody (Fab) heavy and light chains," *Nucleic Acids Research*, 19(15):4133–4137 (1991).

Huse, W.D. et al., "Generation of a Large Combinatorial Library of the Immunoglobulin Repertoire in Phage Lambda," *Science*, 246:1257–1281 (1989).

Huston, J.S. et al., "Protein engineering of antibody binding sites: Recovery of specific activity in an anti–digoxin single–chain Fv analogue produced in *Escherichia coli*," *Proc. Natl. Acad. Sci., USA*, 85:5879–5833 (1988).

Johnston, S, et al., "Interference Between M13 and oriM13 Plasmids is Mediated by a Replication Enhancer Sequence Near the Viral Strand Origin," *J. Molecular Biology*, 177:685–700 (1984).

Kang, A.S. et al., "Linkage of Recognition and Replication Functions by Assembly Combinatorial Antibody Fab Libraries Along Phage Surface," *Proc. Natl. Acad. Sci., USA*, 88(10):4363–4366 (May 15, 1991).

Klauser, T. et al., "Extracellular transport of cholera toxin B subunit using Neisseria IgA protease β–domain: conformation–dependent outer membrane translocation," *EMBO*, 9(6):1991–1999 (1990).

Kornberg, A., in *DNA Replication*, W.H. Freeman and Co., San Francisco, pp. 479–496 (1980).

Landy, A., "Mechanistic and Structural Complexity in the Site–specific Recombination Pathways of Int and FLP," *Current Opinion in Genetics and Development*, 3:699–707 (1993).

Lane, D.P. et al., "Epitope Mapping Using Bacteriophage Peptide Libraries," *Current Opin. Immunol.*, 5:268–271 (1993).

Larrick, J.W. et al., "Rapid Cloning of Rearranged Immunoglobulin Genes from Human Hybridoma CELSS Using Mixed Primers and the Polymerase Chain Reaction," *Biochemical and Biophysical Research Communications*, 160(3):1250–1256 (1989).

Lesk, A. et al., "Elbow motion in the immunoglobulins involves a molecular ball–and–socket joint," *Nature*, 335:188–190 (1988).

Marks, J.D. et al., "By–passing Immunization Human Antibodies from V–gene Libraries Displayed on Phage," *J. Molecular Biology*, 222:581–597 (1991).

Maruyama et al., "A Selective λ Phage Cloning Vector With Automatic Excision of the Insert in a Plasmid," *Gene*, 120:135–141 (1992).

McCafferty, J. et al., "Phage Antibodies: Filamentous Phage Displaying Antibody Variable Domains," *Nature*, 348:552–554 (1990).

Milstein, C., "The Croonian Lecture, 1989. Antibodies: A Paradigm for the Biology of Molecular Recognition," *Proc. R. Soc. London, B. Biol. Sci.*, 239:1–16 (1990).

Neidhardt, F.C. (Ed.), in *Escherichia coli and Salmonella typhimurium, Cellular and Molecular Biology*, American Society of Microbiology, Washington, D.C., pp. 1034–1043, 1054–1060, 1061–1070 (1987).

Ohlson, S. et al., "Novel Approach to Affinity Chromatography Using "Weak" Monoclonal Antibodies," *Analytical Biochemistry*, 169:204–208 (1988).

Orban, P.C. et al., "Tissue– and Site–specific DNA Recombination in Transgenic Mice," *Proc. Natl. Acad. Sci., USA*, 89:6861–6865 (Aug. 1992).

Orlandi, R. et al., "Cloning immunoglobulin variable domains for expression by the polymerase chain reaction," *Proc. Natl. Acad. Sci., USA*, 86:3833–3837 (1989).

Palazzolo, M.J. et al., "Phage Lambda cDNA Cloning Vectors for Subtractive Hybridization, Fusion–protein Synthesis and Cre–loxP Automatic Plasmid Subcloning," *Gene*, 88:25–36 (1990).

Parmley, S.F. et al., "Antibody–selectable Filamentous fd Phage Vectors: Affinity Purification of Target Genes," *Gene* 73(2):305–318 (Dec. 20, 1988).

Parmley, S.F. et al., "Filamentous Fusion Phage Cloning Vectors for the Study of Epitopes and Design of Vaccines," *Adv. Exp. Med. Biol.*, pp. 215–218 (1989).

Peakman, T.C. et al., "Highly Efficient Generation of Recombinant Baculovirus by Enzymatically Mediated site–specific In Vivo Recombination," *Nucleic Acids Research*, 20(3):495–500 (1992).

Pratt, D. et al., "Conditional Lethal Mutants of the Small Filamentous Coliphage M13 II. Two Genes for Coat Proteins," *Virology*, 39:42–53 (1969).

Präve, P., (Ed.), Fundamentals in Biotechnology, VCH, Weinheim, Germany, pp. 307–308 (1987).

Qian, X–H et al., "Reactions between Half– and Full–FLP Recombination Target Sites," *J. Biological Chemistry*, 267(11):7794–7805 (Apr. 15, 1992).

Rathjen, D.A. et al., "Selective enhancement of the tumour necrotic activity of $TNF_\alpha$ with monoclonal antibody," *Br. J. Cancer*, 65:852–856 (1992).

Rosner, J.L., "Formation, Induction and Curing of Bacteriophage P1 Lysogens," *Virology*, 48:679–689 (1972).

Rossomando, E.F. et al., "Studies on the Bacteriophage f1 I. Alkali–induced Disassembly of the Phage into DNA and Protein," *J. Molecular Biology*, 36:387–399 (1968).

Russell et al., "Directed Excision of a Transgene from the Plant Genome," *Mol. Genet. Genet.*, 234:49–59 (1992).

Sambrook et al., "Transformation of *E. coli* by High–voltage Electroporation Electrotransformation," in *Molecular Cloning, A Laboratory Manual*, Second Edition, Cold Spring Harbor Laboratory Press, Cold Spring Harbor, New York, p. 1.75 (1989).

Sambrook, J. et al., in *Molecular Cloning A Laboratory Manual*, Second Edition, Cold Spring Harbor Laboratory Press, Cold Spring Harbor, New York, USA, pp. 5.84, 5.87, 5.88, 13.34, 13.37, 13.39, 13.40, 13.41 and Chapter 15 (1989).

Sastry, L. et al., "Cloning of the immunological repertorie in *Escherichia coli* for generation of monoclonal catalytic antibodies: Construction of a heavy chain variable region–specific cDNA library," *Proc. Natl. Acad. Sci., USA*, 86:5728–5732 (1989).

Short, J.M. et al., "Lambda ZAP: A Bacteriophage Lambda Expression Vector with In Vivo Excision Properties," *Nucleic Acids Research*, 16(15):7583–7600 (Aug. 11, 1988).

Siest, G. et al., "Application of Gene Transfer Technologies to the Production of Enzyme Reference Materials: Example of Gamma–Glutamyltransferase," *Clinical Chemistry*, 39:1573–1589 (1993).

Skerra, A. et al., "Assembly of a Functional Immunoglobulin $F_v$ Fragment in *Escherichia coli*," *Science*, 240:1038–1041 (1988).

Smith, G.P., "Filamentous Fusion Phage: Novel Expression Vectors that Display Coned Antigens on the Virion Surface," *Science*, 228(4705):1315–1317 (Jun. 14, 1985).

Sternberg, N., "Bacteriphage P1 cloning system for the isolation, amplification, and recovery of DNA fragments as large as 100 kilobase pairs," *Proc. Natl. Acad. Sci., USA*, 87:103–107 (1990).

Tsunetsugu–Yokota, Y. et al., "Expression of an Immunogenic Region of HIV by a Filamentous Bacteriophage Vector," *Gene*, 99(2):261–265 (Mar. 15, 1991).

Ward, E.S. et al., "Binding activities of a repertoire of single immunoglobulin variable domains secreted for *Esherichia coli*," *Nature*, 341:544–546 (1989).

Waterhouse, P. et al., "Combinatorial Infection and In Vivo Recombination: A Strategy for Making Large Phage Antibody Repertoires," *Nucleic Acids Research*, 21(9):2265–2266 (1993).

Williams, A.F. et al., "The Immunoglobulin Superfamily–Domains for Cell Surface Recognition," *Annual Review Immunology*, 6:381–405 (1988).

Winter, G. et al., "Man–made Antibodies," *Nature*, 349(6307):293–299 (Jan. 24, 1991).

Zacher, A.N. et al., "A New Filamentous Phage Cloning Vector: fd–tet," *Gene*, 9:127–140 (1980).

Polycombinatorial libraries

Potential library size = $10^{12}$ loxP: ATAACTTCGTATA ATGTATGC TATACGAAGTTAT

Fig. 4B.

```
C kappa
 G  E  C  .  .  .                                                                                                              leader
GGAGAGTTGTTAATAAGGCGCGCCAAAGCTTCCTTAAT ATAACTTCGTATA ATGTATAC TATACGAAGTTAT TAGGTCGCGCATGCAAATTCTATTTCAAGGAGACAGTCATAATGAAA   fdDOG-2lox
          AscI     HindIII                                                                                                     M  K      loxP 511 site
                                                                                                                               (SEQ ID NO: 1)
           IgM CH1                                                                                                             leader
 K  N  V  P  L  P  V  A  A  A  L  N                                                                                            M  K      pUC19-2lox
AACAGCTATGACCATGATTACGCCAAGCTTCCTTAAT ATAACTTCGTATA ATGTATAC TATACGAAGTTAT TAGGTCGCGCATGCAAATTCTATTTCAAGGAGACAGTCATAATGAAA    loxP 511 site
                    HindIII                                                                                                    (SEQ ID NO: 2)
                    NotI
                                                                                                                               fd gene III
                                                                 I  T  S  Y     N  V  C    Y  T  K  L   L  G  L  A  A  E  T  V  E  S  C  L  A  R  P  H
AAAGAACGTGCCCTCTTCCAGTGGGCGGCCGC CTTAAT ATAACTTCGTATA ATGTATGC TATACGAAGTTAT TAGGTCTGGCCGCAGAAACTGTTGAAAGTTGTTAGCAAACCTCAT     fdDOG-2lox
                       NotI                                                                                                    wt loxP site
                                                                                                                               (SEQ ID NO: 4)
                                                                                                                               (SEQ ID NO: 3)
           IgG1 hinge                                                                                    myc Tag
 K  V  D  P  K  S  S  A  A  A  L  N                              I  T  S  Y     N  V  C    Y  T  K  L   L  G  L  A  A  E  Q  R  L  I  S  E  E  D  L  N
GAAAGTTGACCCCAAATCTTCAGCGGCCGCCCTTAAT ATAACTTCGTATA ATGTATGC TATACGAAGTTAT TAGGTCTGGCCGCAGAACAAAAACTCATCTCAGAAGAGGATCTGAAT    pUC19-2lox
                       NotI                                                                                                    wt loxP site
                                                                                                                               (SEQ ID NO: 6)
                                                          loxP site                                                            (SEQ ID NO: 5)
```

METHODS FOR PRODUCING MEMBERS OF SPECIFIC BINDING PAIRS

CROSS REFERENCE TO RELATED APPLICATIONS

This application is a continuation of U.S. patent application Ser. No. 08/307,619, filed Nov. 18, 1994, now U.S. Pat. No. 5,733,743, which was the U.S. National Phase of PCT/GB93/00605, filed Mar. 24, 1993. This application also claims priority of GB application Ser. No. 9206318.9 filed Mar. 24, 1992.

The present invention relates to methods for producing members of specific binding pairs (sbp). In particular, the present invention relates to methods for producing members of specific binding pairs involving recombination between vectors which comprise nucleic acid encoding polypeptide chain components of sbp members.

Structurally, the simplest antibody (IgG) comprises four polypeptide chains, two heavy (H) chains and two light (L) chains inter-connected by disulphide bonds (see FIG. 1). The light chains exist in two distinct forms called kappa (K) and lambda (λ). Each chain has a constant region (C) and a variable region (V). Each chain is organized into a series of domains. The light chains have two domains, corresponding to the C region and the other to the V region. The heavy chains have four domains, one corresponding to the V region and three domains (1,2 and 3) in the C region. The antibody has two arms (each arm being a Fab region), each of which has a VL and a VH region associated with each other. It is this pair of V regions (VL and VH) that differ from one antibody to another (owing to amino acid sequence variations), and which together are responsible for recognising the antigen and providing an antigen binding site (ABS). In even more detail, each V region is made up from three complementarity determining regions (CDR) separated by four framework regions (FR). The CDR's are the most variable part of the variable regions, and they perform the critical antigen binding function. The CDR regions are derived from many potential germ line sequences via a complex process involving recombination, mutation and selection.

It has been shown that the function of binding antigens can be performed by fragments of a whole antibody. Example binding fragments are (i) the Fab fragment consisting of the VL, VH, CL and CH1 domains; (ii) the Fd fragment consisting of the VH and CH1 domains; (iii) the Fv fragment consisting of the VL and VH domains of a single arm of an antibody, (iv) the dAb fragment (Ward, E. S. et al., Nature 341, 544–546 (1989) which consists of a VH domain; (v) isolated CDR regions; and (vi) F(ab')$_2$ fragments, a bivalent fragment comprising two Fab fragments linked by a disulphide bridge at the hinge region.

Although the two domains of the Fv fragment are coded for by separate genes, it has proved possible to make a synthetic linker that enables them to be made as a single protein chain (known as single chain Fv (scFv); Bird, R. E. et al., Science 242, 423–426 (1988) Huston, J. S. et al., Proc. Natl. Acad. Sci., USA 85, 5879–5883 (1988)) by recombinant methods. These scFv fragments were assembled from genes from monoclonals that had been previously isolated.

Bacteriophage have been constructed that express and display at their surface a large biologically functional binding molecule (eg antibody fragments, and enzymes and receptors) and which remain intact and infectious. This is described in WO 92/01047, the disclosure of which is herein incorporated by reference. Readers of the present document are urged to consult WO 92/01047 for detailed explanation of many of the procedures used in the experiments described herein. The applicants have called the structure which comprises a virus particle and a binding molecule displayed at the viral surface a 'package'. Where the binding molecule is an antibody, an antibody derivative or fragment, or a domain that is homologous to an immunoglobulin domain, the applicants call the package a 'phage antibody' (pAb). However, except where the context demands otherwise, where the term phage antibody is used generally, it should also be interpreted as referring to any package comprising a virus particle and a biologically functional binding molecule displayed at the viral surface.

pAbs have a range of applications in selecting antibody genes encoding antigen binding activities. For example, pAbs could be used for the cloning and rescue of hybridomas (Orlandi, R., et al (1989) PNAS 86 p3833–3837), and in the screening of large combinatorial libraries (such as found in Huse, W.D. et al., 1989, Science 246, 1275–1281). In particular, rounds of selection using pAbs may help in rescuing the higher affinity antibodies from the latter libraries. It may be preferable to screen small libraries derived from antigen-selected cells (Casali, P., et al., (1986) Science 234 p476–479) to rescue the original VH/VL pairs comprising the Fv region of an antibody. The use of pAbs may also allow the construction of entirely synthetic antibodies. Furthermore, antibodies may be made which have some synthetic sequences e.g. CDRs, and some naturally derived sequences. For example, V-gene repertoires could be made in vitro by combining unrearranged V genes, with D and J segments. Libraries of pAbs could then be selected by binding to antigen, hypermutated in vitro in the antigen-binding loops or V domain framework regions, and subjected to further rounds of selection and mutagenesis.

The demonstration that a functional antigen-binding domain can be displayed on the surface of phage, has implications beyond the construction of novel antibodies. For example, if other protein domains can be displayed at the surface of a phage, phage vectors could be used to clone and select genes by the binding properties of the displayed protein. Furthermore, variants of proteins, including epitope libraries built into the surface of the protein, could be made and readily selected for binding activities. In effect, other protein architectures might serve as "nouvelle" antibodies.

The technique provides the possibility of building antibodies from first principles, taking advantage of the structural framework on which the antigen binding loops fold. In general, these loops have a limited number of conformations which generate a variety of binding sites by alternative loop combinations and by diverse side chains. Recent successes in modelling antigen binding sites augurs well for de novo design. In any case, a high resolution structure of the antigen is needed. However, the approach is attractive for making e.g. catalytic antibodies, particularly for small substrates. Here side chains or binding sites for prosthetic groups might be introduced, not only to bind selectively to the transition state of the substrate, but also to participate directly in bond making and breaking. The only question is whether the antibody architecture, specialised for binding, is the best starting point for building catalysts. Genuine enzyme architectures, such as the triose phosphate isomerase (TIM) barrel, might be more suitable. Like antibodies, TIM enzymes also have a framework structure (a barrel of β-strands and α-helices) and loops to bind substrate. Many enzymes with a diversity of catalytic properties are based on this architecture and the loops might be manipulated independently on the frameworks for design of new catalytic and binding properties. The phage selection system as provided by the present disclosure can be used to select for antigen binding activities and the CDR loops thus selected, used on either an antibody framework or a TIM barrel framework. Loops placed on a e.g. a TIM barrel framework could be further modified by mutagenesis and subjected to further selection. Thus, there is no need to select for high affinity binding activities in a single step. The strategy of the immune system, in which low affinity evolves to high affinity seems more realistic and can be mimicked using this invention.

One class of molecules that could be useful in this type of application are receptors. For example, a specific receptor could be displayed on the-surface of the phage such that it would bind its ligand. The receptor could then be modified by, for example, in vitro mutagenesis and variants having higher binding affinity for the ligand selected. The selection may be carried out according to one or more of the formats described below.

Alternatively, the phage-receptor could be used as the basis of a rapid screening system for the binding of ligands, altered ligands, or potential drug candidates. The advantages of this system namely of simple cloning, convenient expression, standard reagents and easy handling makes the drug screening application particularly attractive. In the context of this discussion, receptor means a molecule that binds a specific, or group of specific, ligand(s). The natural receptor could be expressed on the surface of a population of cells, or it could be the extracellular domain of such a molecule (whether such a form exists naturally or not), or a soluble molecule performing a natural binding function in the plasma, or within a cell or organ.

Another possibility, is the display of an enzyme molecule or active site of an enzyme molecule on the surface of a phage (see examples 11,12,30,31,32 and 36 of WO 92/01047). Once the phage enzyme is expressed, it can be selected by affinity chromatography, for instance on columns derivatized with transition state analogues. If an enzyme with a different or modified specificity is desired, it may be possible to mutate an enzyme displayed as a fusion on bacteriophage and then select on a column derivatised with an analogue selected to have a higher affinity for an enzyme with the desired modified specificity.

Although throughout this application, the applicants discuss the possibility of screening for higher affinity variants of pAbs, they recognise that in some applications, for example low affinity chromatography (Ohlson, S. et al Anal. Biochem. 169, p204–208 (1988)), it may be desirable to isolate lower affinity variants.

pAbs also allow the selection of antibodies for improved stability. It has been noted for many antibodies, that yield and stability are improved when the antibodies are expressed at 30° C. rather than 37° C. If pAbs are displayed at 37° C., only those which are stable will be available for affinity selection. When antibodies are to be used in vivo for therapeutic or diagnostic purposes, increased stability would extend the half-life of antibodies in circulation.

Although stability is important for all antibodies and antibody domains selected using phage, it is particularly important for the selection of Fv fragments which are formed by the non-covalent association of VH and VL fragments. Fv fragments have a tendency to dissociate and have a much reduced half-life in circulation compared to whole antibodies. Fv fragments are displayed on the surface of phage, by the association of one chain expressed as a gene III protein fusion with the complementary chain expressed as a soluble fragment. If pairs of chains have a high tendency to dissociate, they will be much less likely to be selected as pAbs. Therefore, the population will be enriched for pairs which do associate stably. Although dissociation is less of a problem with Fab fragments, selection would also occur for Fab fragments which associate stably. pAbs allow selection for stability to protease attack, only those pAbs that are not cleaved by proteases will be capable of binding their ligand and therefore populations of phage will be enriched for those displaying stable antibody domains.

The technique of displaying binding molecules on the phage surface can also be used as a primary cloning system. For example, a cDNA library can be constructed and inserted into the bacteriophage and this phage library screened for the ability to bind a ligand. The ligand/binding molecule combination could include any pair of molecules with an ability to specifically bind to one another e.g. receptor/ligand, enzyme/substrate (or analogue), nucleic acid binding protein/nucleic acid etc. If one member of the complementary pair is available, this may be a preferred way of isolating a clone for the other member of the pair.

The first functional antibody molecules to be expressed on the surface of filamentous phage were single-chain Fv's (scFv), so-called because heavy and light chain variable domains, normally on two separate proteins, are covalently joined by a flexible linker peptide. Alternative expression strategies have also been successful. Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each fab molecule assemble post-translationally and the dimer is incorporated into the phage particle via linkage of one of the chains to g3p.

More recent cloning has been performed with 'phagemid' vectors which have ca. 100-fold higher transformation efficiencies than phage DNA. These are plasmids containing the intergenic region from filamentous phages which enables single-stranded copies of the phagemid DNA to be produced, and packaged into infectious filamentous particles when cells harbouring them are infected with 'helper' phages providing the phage components in trans. When phagemids contain gIII fused to an antibody gene (eg pHEN-1), the resulting fusion protein is displayed on the phagemid particle (Hoogenboom, H. R., A. D. Griffiths, K. S. Johnson, D. J. Chiswell, P. Hudson and G. Winter. (1991). Multi-subunit proteins on the surface of filamentous phage: methodologies for displaying antibody (Fab) heavy and light chains. Nucleic Acids Res. 19 (15), 4133–4137). Efficient strategies have been developed for cloning antibody genes, a factor which becomes most important when dealing with large numbers of different antibody fragments such as repertoires.

The cloning vector fd-DOG-1 was used in early work with phage antibody repertoires in which scFv fragments were derived from spleen mRNA of mice immunised with the hapten oxazalone (Clackson, T., H. R. Hoogenboom,. A. D. Griffiths and G. Winter. (1991). Making antibody fragments using phage display libraries. Nature. 352, 624–628.); VH and VL domains were separately amplified then linked at random via a short DNA fragment encoding the scFv linker peptide to produce a library of approxiamtely $10^5$ different clones. This was panned against the immunising antigen to select combinations of VH and VL which produced functional antibodies. Several binders were isolated, one in particular having an affinity not far below that of the best monoclonal antibodies produced by conventional hybridoma technology.

In a mouse, at any one time there are approximately $10^7$ possible H chains and $10^5$ possible L chains, making a total of $10^{12}$ possible VH:VL combinations when the two chains are combined at random (these figures are estimates and simply provide a rough guide to repertoire size). By these figures, the above mouse library sampled only 1 in $10^7$ of the possible VH:VL combinations. It is likely that good affinity antibodies were isolated in the work described in the preceeding paragraph because the spleen cells derived from an immunised donor in which B cells capable of recognising the antigen are clonally expanded and producing large quantities of Ig MRNA. The low library complexity in this experiment is partly due to the intrinsically low transformation efficiency of phage DNA compared to plasmid (or phagemid).

Marks et al. (Marks, J. D., Hoogenboom, H. R., Bonnert, T. P., McCafferty, J., Griffiths, A. D. and Winter, G. (1991) By-passing immunization: Human antibodies from V-gene libraries displayed on phage. J. Mol. Biol. 222, 581–597) and W092/01047 describe construction of an antibody repertoire from unimmunised humans cloned in the phagemid pHEN-1. This library, consisting of $3.01^7$ clones has so far yielded specific antibodies to many different antigens. These antibodies tend to have the moderate affinities expected of a primary immune response, demonstrating that usable antibodies to a range of structurally diverse antigens can indeed be isolated from a single resource.

New binders can be created from clones isolated from phage antibody libraries using a procedure called 'chain-shuffling'. In this process one of the two chains is fixed and the other varied. For example, by fixing the heavy chain from the highest affinity mouse anti-OX phage antibody and recloning the repertoire of light chains alongside it, libraries of $4.10^7$ were constructed. Several new OX-binders were isolated, and the majority of these had light chains that were distinct from those first isolated and considerably more diverse. These observations reflect the fact that a small library is sufficient to tap the available diversity when only one chain is varied, a useful procedure if the original library was not sufficiently large to contain the available diversity.

The size of the library is of critical importance. This is especially true when attempting to isolate antibodies from a naive human repertoire, but is equally relevant to isolation of the highest affinity, antibodies from an immunised source.

It is clear that while phage display is an exceptionally powerful tool for cloning and selecting antibody genes, we are tapping only the tiniest fraction of the potential diversity using existing technology. Transformation efficiencies place the greatest limitation on library size with $10^9$ being about the limit using current methods. Rough calculations suggest that this is several orders of magnitude below the target efficiency; more rigourous analysis confirms it.

Perelson and Oster have given theoretical consideration to the relationship between size of the immune repertoire and the likelihood of generating an antibody capable recognising a given epitope with greater than a certain threshold affinity, K. The relationship is described by the equation:

$$P = e^{-N(p[k])}$$

Where P=probability that an epitope is not recognised with an affinity above the threshold value K by any antibody in the repertoire, N=number of different antibodies in the repertoire, and p[K]=probability that an individual antibody recognises a random epitope with an affinity above the threshold value K In this analysis p[K] is inversely proportional to affinity, although an algorithm describing this relationship precisely has not been deduced. Despite this, it is apparent that the higher the affinity of the antibody, the lower its p[K] and the larger the repertoire needs to be to achieve a reasonable probability of isolating that antibody. The other important feature is that the function is exponential; as shown in FIG. 1, a small change in library size can have either a negligible or a dramatic effect on the probability of isolating an antibody with a given p[K] value, depending upon what point on the curve is given by the library size.

WO 92/01047 and W092/20791 describe how the limitations of transformation efficiency (and therefore the upper limit on library size) can be overcome by use of other methods for introducing DNA into cells, such as infection. In one configuration, heavy and light chain genes are cloned separately on two different replicons, at least one of which is capable of being incorporated into a filamentous particle. Infectious particles carrying one chain are infected into cells harbouring the complementary chain; infection frequencies of >90% can be readily achieved. Heavy and light chains are then able to associate post-translationally in the periplasm and the combination displayed on the surface of the filamentous particle by virtue of one or both chains being connected to g3p. For example, a library of $10^7$ heavy chains is cloned as an unfused population in a phagemid, and $10^7$ light chains are cloned as g3 fusions in fd-DOG-1. Both populations are then expanded by growth such that there are $10^7$ of each heavy chain-containing cell and $10^7$ copies of each light chain phage. By allowing the phage to infect the cells, $10^7 \times 10^7 = 10^{14}$ unique combinations can be created, because there are $10^7$ cells carrying the same heavy chain which can each be infected by $10^7$ phage carrying different light chains. When this is repeated for each different heavy chain clone then one ends up with up to $10^{14}$ different heavy/light combinations in different cells. This strategy is outlined in FIG. 2, which shows the heavy chain cloned as g3 fusions on phage and the light chains expressed as soluble fragments from a phagemid. Clearly, the reverse combination, light chains on phage, heavy chain on phagemid, is also tenable.

In the configuration shown in FIG. 2, fd-DOG 'rescues' the phagemid so that both phage and phagemid DNA is packaged into filamentous particles, and both types will have paired heavy and light chains on their surface, despite having the genetic information for only one of them. For a given antigen or epitope, the vast majority of the heavy and light chain pairings will be non-functional (ie. will not bind that antigen or epitope), so that selection on antigen will have the effect of vastly reducing the complexity of the heavy and light chain populations. After the first round of selection the clones are re-assorted, for example by infecting fresh host cells and selecting for both replicons. After several rounds of antigen selection and recovery of the two replicons, the considerably reduced heavy and light chain populations can be cloned onto the same replicon and analysed by conventional means. Selection from the, say, $10^{14}$ combinations produces a population of phages displaying a particular combination of H and L chains having the desired specificity. The phages selected however, will only contain DNA encloding one partner of the paired H and L chains. Selection for the two replicons may be as follows. Vectors of the H chain library may encode tetracycline resistance, with vectors of the L chain library encoding ampicillin resistance. The sample elute containing the population is divided into two portions. A first portion is grown on e.g. tetracycline plates to select those bacteriophage containing DNA encoding H chains which are involved in the desired antigen binding. A second portion is grown on e.g. ampicillin plates to select those bacteriophage containg phagemid DNA encoding L chains which are involved in the desired antigen binding. A set of colonies from individually isolated clones e.g. from the tetracycline plates are then used to infect specific colonies e.g. from the ampicillin plates. This results in bacteriophage expressing specific combinations of H and L chains which can then be assayed for antigen binding.

One technical problem with the use of separate eplicons for VL and VH chains is so-called 'interference' between filamentous phage origins of replication carried on different replicons as a result of competition for the same replication machinery.

Procedures have been described which work on the principle of first reducing the complexity of a repertoire then recloning one or both chains of the reduced population (WO92/20791). The present invention provides a different approach.

TERMINOLOGY

Much of the terminology discussed in this section has been mentioned in the text where appropriate.

Specific Binding Pair (sbp)

This describes a pair of molecules (each being a member of a specific binding pair) which are naturally derived or synthetically produced. One of the pair of molecules, has an area on its surface, or a cavity which specifically binds to, and is therefore defined as complementary with a particular spatial and polar organisation of the other molecule, so that the pair have the property of binding specifically to each other. Examples of types of specific binding pairs are antigen-antibody, biotin-avidin, hormone-hormone receptor, receptor-ligand, enzyme-substrate, lgG-protein A.

Multimeric Member

This describes a first polypeptide which will associate with at least a second polypeptide, when the polypeptides are expressed in free form and/or on the surface of a substrate. The substrate may be provided by a bacteriophage. Where there are two associated polypeptides, the associated polypeptide complex is a dimer, where there are three, a trimer etc. The dimer, trimer, multimer etc or the multimeric member may comprise a member of a specific binding pair.

Example multimeric members are heavy domains based on an immunoglobulin molecule, light domains based on an immunoglobulin molecule, T-cell receptor subunits.

Replicable Genetic Display Package (Rgdp)

This describes a biological particle which has genetic information providing the particle with the ability to replicate. The particle can display on its surface at least part of a polypeptide. The polypeptide can be encoded by genetic information native to the particle and/or artificially placed into the particle or an ancestor of it. The displayed polypeptide may be any member of a specific binding pair eg. heavy or light chain domains based on an immunoglobulin molecule, an enzyme or a receptor etc.

The particle may be a virus eg. a bacteriophage such as fd or M13.

Package

This describes a replicable genetic display package in which the particle is displaying a member of a specific binding pair at its surface. The package may be a bacteriophage which displays an antigen binding domain at its surface. This type of package has been called a phage antibody (pAb).

Antibody

This describes an immunoglobulin whether natural or partly or wholly synthetically produced. The term also covers any protein having a binding domain which is homologous to an immunoglobulin binding domain. These proteins can be derived from natural sources, or partly or wholly synthetically produced.

Example antibodies are the immunoglobulin isotypes and the Fab, $F(ab^1)_2$, scFv, Fv, dAb, Fd fragments.

Immunoglobulin Superfamily

This describes a family of polypeptides, the members of which have at least one domain with a structure related to that of the variable or constant domain of immunoglobulin molecules. The domain contains two β-sheets and usually a conserved disulphide bond (see A. F. Williams and A. N. Barclay 1988 Ann. Rev Immunol. 6 381–405).

Example members of an immunoglobulin superfamily are CD4, platelet derived growth factor receptor (PDGFR), intercellular adhesion molecule. (ICAM). Except where the context otherwise dictates, reference to immunoglobulins and immunoglobulin homologs in this application includes members of the immunoglobulin superfamily and homologs thereof.

Homologs

This term indicates polypeptides having the same or conserved residues at a corresponding position in their primary, secondary or tertiary structure. The term also extends to two or more nucleotide sequences encoding the homologous polypeptides.

Example homologous peptides are the immunoglobulin isotypes.

Functional

In relation to a sbp member displayed on the surface of a rgdp, means that the sbp member is presented in a folded form in which its specific binding domain for its complementary sbp member is the same or closely analogous to its native configuration, whereby it exhibits similar specificity with respect to the complementary sbp member. In this respect, it differs from the peptides of Smith et al, supra, which do not have a definite folded configuration and can assume a variety of configurations determined by the complementary members with which they may be contacted.

Genetically Diverse Population

In connection with sbp members or polypeptide components thereof, this is referring not only to diversity that can exist in the natural population of cells or organisms, but also diversity that can be created by artificial mutation in vitro or in vivo.

Mutation in vitro may for example, involve random mutagenesis using oligonucleotides having random mutations of the sequence desired to be varied. In vivo mutagenesis may for example, use mutator strains of host microorganisms to harbour the DNA (see Example 38 of WO92/01047). The word "population" itself may be used to denote a plurality of e.g. polypeptide chains, which are not genetically diverse i.e. they are all the same.

Domain

A domain is a part of a protein that is folded within itself and independently of other parts of the same protein and independently of a complementary binding member.

Folded Unit

This is a specific combination of an α-helix and/or β-strand and/or β-turn structure. Domains and folded units contain structures that bring together amino acids that are not adjacent in the primary structure.

Free Form

This describes the state of a polypeptide which is not displayed by a replicable genetic display package.

Conditionally Defective

This describes a gene which does not express a particular polypeptide under one set of conditions, but expresses it under another set of conditions. An example, is a gene containing an amber mutation expressed in non-suppressing or suppressing hosts respectively.

Alternatively, a gene may express a protein which is defective under one set of conditions, but not under another set. An example is a gene with a temperature sensitive mutation.

Suppressible Translational Stop Codon

This describes a codon which allows the translation of nucleotide sequences downstream of the codon under one set of conditions, but under another set of conditions translation ends at the codon. Example of suppressible translational stop codons are the amber, ochre and opal codons.

Mutator Strain

This is a host cell which has a genetic defect which causes DNA replicated within it to be mutated with respect to its parent DNA. Example mutator strains are NR9046mutD5 and NR9046 mut T1 (see Example 38).

Helper Phage

This is a phage which is used to infect cells containing a defective phage genome and which functions to complement the defect. The defective phage genome can be a phagemid or a phage with some function encoding gene sequences removed. Examples of helper phages are M13KO7, M13KO7 gene III no. 3; and phage displaying or encoding a binding molecule fused to a capsid protein.

Vector

This is a DNA molecule, capable of replication in a host organism, into which a gene is inserted to construct a recombinant DNA molecule.

Phage Vector

This is a vector derived by modification of a phage genome, containing an origin of replication for a bacteriophage, but not one for a plasmid.

Phagemid Vector

This is a vector derived by modification of a plasmid genome, containing an origin of replication for a bacteriophage as well as the plasmid origin of replication.

Secreted

This describes a rgdp or molecule that associates with the member of a sbp displayed on the rgdp, in which the sbp member and/or the molecule, have been folded and the package assembled externally to the cellular cytosol.

Repertoire of Rearranged Immunoglobulin Genes

A collection of naturally occurring nucleotides, eg DNA sequences which encoded expressed immunoglobulin genes in an animal. The sequences are generated by the in vivo rearrangement of eg V, D and J segments for H chains and eg the V and J segments for L chains. Alternatively the sequences may be generated from a cell line immunised in vitro and in which the rearrangement in response to immunisation occurs intracellularly. The word "repertoire" is used to indicate genetic diversity.

Library

A collection of nucleotide eg DNA, sequences within clones; or a genetically diverse collection of polypeptides, or specific binding pair members, or polypeptides or sbp members displayed on rgdps capable of selection or screening to provide an individual polypeptide or sbp members or a mixed population of polypeptides or sbp members.

Repertoire of Artificially Rearranged Immunoglobulin Genes

A collection of nucleotide eg DNA, sequences derived wholly or partly from a source other than the rearranged immunoglobulin sequences from an animal. This may include for example, DNA sequences encoding VH domains by combining unrearranged V segments with D and J segments and DNA sequences encoding VL domains by combining V and J segments.

Part or all of the DNA sequences may be derived by oligonucleotide synthesis.

Secretory Leader Peptide

This is a sequence of amino acids joined to the N-terminal end of a polypeptide and which directs movement of the polypeptide out of the cytosol.

Eluant

This is a solution used to breakdown the linkage between two molecules. The linkage can be a noncovalent or covalent bond(s). The two molecules can be members of a sbp.

Derivative

This is a substance which derived from a polypeptide which is encoded by the DNA within a selected rgdp. The derivative polypeptide may differ from the encoded polypeptide by the addition, deletion, substitution or insertion of amino acids, or by the linkage of other molecules to the encoded polypetide. These changes may be made at the nucleotide or protein level. For example the encoded polypeptide may be a Fab fragment which is then linked to an Fc tail from another source. Alternatively markers such as enzymes, flouresceins etc may be linked to eg Fab, scFv fragments.

According to one aspect of the present invention there is provided a method for producing multimeric specific binding pair (sbp) members, which method comprises causing or allowing recombination between (a) first vectors comprising nucleic acid encoding a population of a fusion of a first polypeptide chain of a specific binding pair member and a component of a replicable genetic display package (rgdp) and (b) second vectors comprising nucleic acid encoding a population of a second polypeptide chain of a specific binding pair member, at least one of said populations being genetically diverse, the recombination resulting in recombinant vectors each of which comprises nucleic acid encoding a said polypeptide fusion and a said second polypeptide chain and capable of being packaged into rgdps using said rgdp component.

One or other or both of the populations of first and second polypeptide chains may be genetically diverse. Where both are genetically diverse, the recombinant vectors will represent an enormously diverse repertoire of sbp members. Either or both of the populations may be genetically diverse but restricted compared with the full repertoire available, perhaps by virtue of a preceding selection or screening step. A library of nucleic acid encoding a restricted population of polypeptide chains may be the product of selection or screening using rgdp display.

According to another aspect of the invention there is provided a method of producing multimeric specific binding pair (sbp) members, which method comprises:

(i) expressing from a vector in recombinant host organism cells a population of a first polypeptide chain of a specific binding pair member fused to a component of a replicable genetic display package (rgdp) which thereby displays said polypeptide chains at the surface of rgdps, and combining said population with a population of a second polypeptide chain of said specific binding pair member by causing or allowing first and second polypeptide chains to come together to form a library of said multimeric specific binding pair members displayed by rgdps, said population of second polypeptide chains not being expressed from the same vector as said population of first polypeptide chains, at least one of said populations being genetically diverse and expressed from nucleic acid that is capable of being packaged using said rgdp component, whereby the genetic material of each said rgdp encodes a polypeptide chain of a said genetically diverse population;

(ii) selecting or screening rgdps formed by said expressing to provide an individual sbp member or a mixed population of said sbp members associated in their respective rgdps with nucleic acid encoding a polypeptide chain thereof;

(iii) obtaining nucleic acid from a selected or screened rgdp, the nucleic acid obtained being one of (a) nucleic acid encoding a first polypeptide chain, (b) nucleic acid encoding a second polypeptide chain, and (c) a mixture of (a) and (b);

(iv) producing a recombinant vector by causing or allowing recombination between (a) a sector comprising nucleic acid obtained in step (iii) encoding a first polypeptide chain and a vector comprising nucleic acid encoding a second polypeptide chain, or (b) a vector comprising nucleic acid encoding a first polypeptide chain and a vector comprising nucleic acid obtained in step (iii) encoding a second polypeptide chain.

The recombination may take place intracellularly or in vitro, although it is preferable that it takes place in recombinant host cells. This is discussed elsewhere, but briefly this may involve introducing a library of vectors including nucleic acid encoding first (or second) polypeptide chain components of sbp member into host cells harbouring a library of vectors comprising nucleic acid encoding second (or first) polypeptide chain components of sbp members.

Following the recombination the polypeptide fusions (first polypeptide chains fused to a rgdp component) and the second polypeptide chains may be expressed, producing rgdps which display at their surface said first and second polypeptide chains and which each comprise nucleic acid encoding a said first polypeptide chain and a said second polypeptide chain, by virtue of the packaging of the recombinant vectors into rgdps. This expression may therefore produce an extremely diverse library of sbp members displayed on rgdp. In one embodiment, the rgdps displaying sbp member are pAbs (ie phage displaying antibodies or antibody fragments or derivatives), and those which bind antigen of interest may be selected using their binding capability. Since each pAb contains within it nucleic acid encoding both polypeptide chains of the antibody displayed on its surface, pAbs selected by binding to an antigen of interest will provide nucleic acid encoding an antibody which binds that antigen. The nucleic acid may be isolated from the selected pAbs and used in subsequent obtention of desired antibodies, after any amplification and cloning required in a given case.

The recombination may be promoted by inclusion in the vectors of sequences at which site-specific recombination will occur. This enables accurate design of the resultant recombinant vectors. For instance, a sequence at which site-specific recombination will occur may be position in the nucleic acid which encodes a polypeptide linker which joins the two domains of a single chain sbp member. The single chain sbp member may consist of an immunoglobulin VH domain linked to an immunoglobulin VL domain. VH and VL domains may associate to form an antigen binding site. The resultant recombinant vector may then comprise nucleic acid encoding a single chain Fv derivative of an immunoglobulin resulting from recombination between first and second vectors. (Note: a single chain sbp member, such as a scFv fragment or derivative of an antibody, may be considered to be multimeric (dimeric) because it consists of two polypeptide chain domains, such as VL and VH of an antibody.)

The sequences at which site-specific recombination will occur may be loxP sequences obtainable from coliphage P1, with site-specific recombination catalysed by Cre-recombinase, also obtainable from coliphage P1. The site-specific recombination sequences used may be derived from a loxP sequence obtainable from coliphage P1.

The Cre-recombinase used may be expressible under the control of a regulatable promoter.

In order to increase the efficiency of the method, increasing the proportion of productive recombination leading to the resultant recombinant vectors desired, each vector may include two site-specific recombination sequences each of which is different from the other. The sequences should then be such that recombination will take place between like sequences on different vectors but not between the different sequences on the same vector.

Each of the first vectors and each of the second vectors may include a first site-specific recombination sequence and a second site-specific recombination sequence different from the first, site-specific recombination taking place between first site-specific recombination sequences on different vectors and between second site-specific recombination sequences on different vectors but not between a first site-specific recombination sequence and a second site-specific recombination sequence on the same vector.

The first site-specific recombination sequence may be loxP obtainable from coliphage P1 and the second site-specific recombination sequence a mutant loxP sequence, or vice versa. Potentially, both the first and second site-specific recombination sequences may be mutants, as long as the first sequence will not recombine with the second sequence but first sequences will recombine with each other and second sequences will recombine with each other.

A suitable mutant loxP sequence is loxP 511.

The first vectors may be phages or phagemids and the second vectors plasmids, or the first vectors may be plasmids and the second vectors phages or phagemids.

In one embodiment, the recombination is intracellular and takes place in a bacterial host which replicates the recombinant vector preferentially over the first vectors and the second vectors. This may be used to enrich selection of successful recombination events. The intracellular recombination may take place in a bacterial host which replicates plasmids preferentially over phages or phagemids, or which replicates phages or phagemids preferentially over plasmids. For instance, the bacterial host may be a PolA strain of *E.coli* or of another gram-negative bacterium. PolA cells are unable to support replication of plasmids, but can support replication of filamentous phage and phagemids (plasmids containing filamentous phage intergenic regions). So, for instance, if the first vectors are plasmids containing a first marker gene, and the second vectors are phage or phagemids containing a second marker gene, selection for both markers will yield recombinant vectors which are the product of a successful recombination event, since recombination transferring the first marker from plasmid must take place in order for that marker to be replicated and expressed.

Nucleic acid from one or more rgdp's may be taken and used in a further method to obtain an individual sbp member or a mixed population of sbp members, or polypeptide chain components thereof, or encoding nucleic acid therefor.

The present invention also provides a kit for use in carrying out methods provided, having:

(i) a first vector having a restriction site for insertion of nucleic acid encoding or a polypeptide component of an sbp member, said restriction site being in the 5' end region of the mature coding sequence of a phage capsid protein, with a secretory leader sequence upstream of said site which directs a fusion of the capsid protein and sbp polypeptide to the periplasmic space of a bacterial host; and (ii) a second vector having a restriction site for insertion of nucleic acid encoding a second said polypeptide chain,
at least one of the vectors having an origin of replication for single-stranded bacteriophage, the vectors having sequences at which site-specific recombination will occur.

The kit may contain ancillary components needed for working the method.

Also provided by the present invention are recombinant host cells harbouring a library of first vectors each comprising nucleic acid encoding a first polypeptide chain of a sbp member fused to a component of a secretable replicable genetic display package (rgdp) and second vectors each comprising nucleic acid encoding a second polypeptide chain of a sbp member, the first vectors or the second vectors or both being capable of being packaged into rgdps using the rgdp component, and the vectors having sequences at which site-specific recombination will occur.

According to another aspect of the present invention there is providedn a population of rgdps each displaying at its surface a sbp member and each containing nucleic acid which encodes a first and a second polypeptide chain of the sbp member displayed at its surface and which includes a site-specific recombination sequence.

According to another aspect of the invention there is provided a population of rgdps each displaying at its surface a sbp member and each containing nucleic acid which comprises a combination of (i) nucleic acid encoding a first polypeptide chain of a sbp member and (ii) nucleic acid encoding a second poypeptide chain of a sbp member, the population containing $10^{10}$ or more combinations of (i) and (ii). Such a population exceeds in size the maximum which is achievable using available techniques. The present invention enables production of enormously diverse libraries or populations of rgdps displaying sbp members. The nucleic acid encoding a first polypeptide chain of a sbp member may have, for instance, $10^7$ different sequences throughout the population. Where the nucleic acid encoding a second polypeptide chain of a sbp member also has such a genetic diversity throughout the population, the number of different combinations of nucleic acid encoding first and second polypeptide chains is immense.

Embodiments of the present invention will now be described in more detail by way of example only and not by way of limitation, with reference to the figures.

BRIEF DESCRIPTION OF THE FIGURES

FIG. 4A–FIG. 4A-1 shows replicons generated by Cre mediated recombination between the acceptor phage vector fdDOG-2lox (A) and the donor plasmid vector pUC19-2lox (B). A is based on fd-tet-DOG1, with Vk from the mouse anti-phox antibody NQ10.12.5 linked to a human Ck constant domain, and VH from the mouse anti-TNFa antibody linked to a human Cm1 constant domain. B is based on pUC19, with VH of NQ10.12.5 linked to the human Cg1 constant domain. Within *E. coli* an equilibrium between the six vectors develops due to the reversible nature of recombination in the lox-Cre system. Ribosome-binding sites (small open circles), c-myc peptide tag (myc), phage fd gene III leader peptide sequence (Lg3), pelB leader peptide sequence (LpelB), fd phage gene III (gIII) and locations of oligonucleotides used for hybridisation and screening are indicated.

FIG. 4B shows the sequence across the wild-type loxP and mutant loxP 511 sites present in fdDOG-2lox (A) (SEQ ID NOS: 1, 3, & 4) and pUC19-2lox (B) (SEQ ID NOS: 2, 5 & 6). The inverted repeats in the loxP sites are boxed and the position of the point mutation in the mutant loxP 511 site is indicated (#), as are the ribosome-binding sites (r.b.s.). Note that the wild-type loxP sites are in frame to ensure that the heavy chains immediately upstream can be fused to gene III for display on phage.

Figure 1:
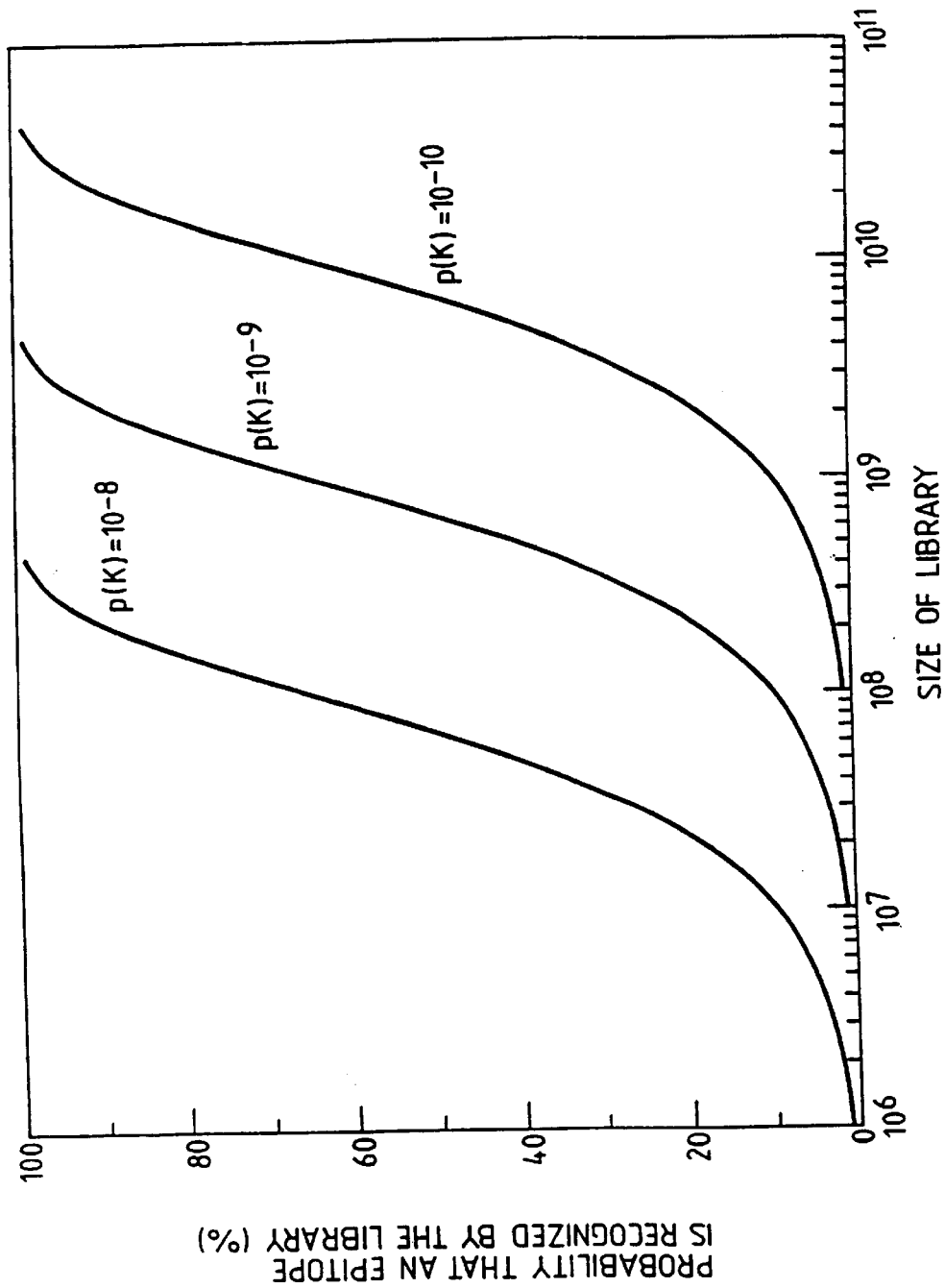
FIG. 1 shows plots of the probability of isolating an antibody with a given p[K] value against the size of a library.
Figure 2:
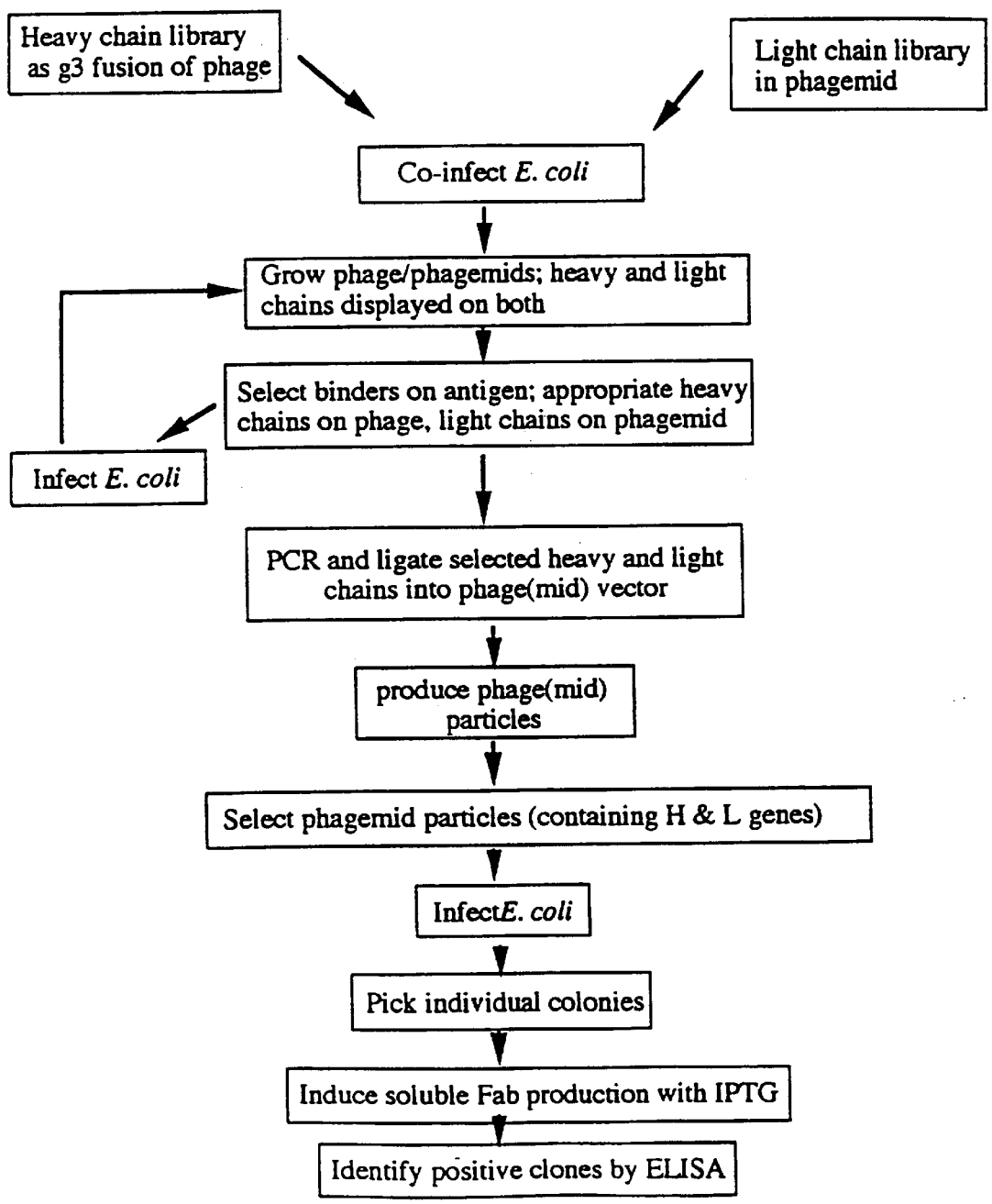
FIG. 2 outlines a strategy to clone heavy chain as g3 fusion on phage, light chain being expressed as soluble fragments from a phagemid.

Disclosed here are methods useful for preparing extremely diverse libraries of specific binding pair members, such as antibody heavy and light chains. Heavy and light chains cloned on separate replicons may be introduced into host cells. The heavy and light chain genes are recombined onto the same replicon such that the final number of combinations created is the number of heavy chains multiplied by the number of light chains. Recombination can occur in vivo or in vitro. Preferably, the recipient replicon is capable of being incorporated into an rgdp such that functional combinations of heavy and light chain genes can be selected. Such a format is particularly advantageous for construction of extremely diverse libraries of antibody heavy and light chains, for example, from unimmunised donors, immunised donors or a repertoire of an artificially rearranged immunoglobulin gene or genes, and is also convenient for chain-shuffling, mutagenesis, humanising and CDR 'imprinting'.

These methods can also be applied to other proteins in which two or more subunits assemble to create a functional oligomer.

The genes for both subunits present on two separate replicons can be brought together onto the same rgdp such that favourable combinations of subunit genes may be isolated directly without recourse to extensive recloning. This may be achieved by recombination between the replicons once they have been introduced into the same cell. In a preferred configuration, recombination events are effected such that the genes for one of the chains is recombined onto a recipient replicon which contains the gene for a partner chain. Preferably, the recipient replicon is capable of being packaged into an rgdp. Most preferably, the genes encoding one or more of the subunits is fused to a capsid gene such as gIII in order that the functional multimer can be displayed on the surface of the rgdp.

A variety of recombination systems are known, and many of these could be harnessed in such a way as to effect recombination between replicons. Example recombination systems include general recombination, transposition and site-specific recombination.

General recombination is a process whereby genetic exchange occurs between DNA segments that share some homology, and is also known as 'homologous recombination'. It is the principal mechanism by which genetic material is transferred between chromosomes, and in *E.coli* the process is catalysed by the rec BCD enzyme (In *"Escherichia coli* and Salmonella typhimurium.

Cellular and Molecular Biology."(1987). pp1034–1043. Neidhart, F. C. Editor in Chief. American Society for Microbiology). A general recombination mechanism could be used to transfer genes from one replicon to the other if, for example, the rgdp genome has a gene for one of the chains and a 'dummy' partner chain gene such that recombination would have to occur to replace the dummy gene on the rgdp replicon with the functional gene on the second replicon in order to produce a functional pairing.

Transposition could also be used to effect transfer of genetic information from one replicon to another (In *"Escherichia coli* and *Salmonella typhimurium*. Cellular and Molecular Biology." (1987). pp10661–1070. Neidhart, F. C. Editor in Chief. American Society for Microbiology). Transposons such as Tn 3 and Tn 10 are DNA segments that have also been called 'jumping genes' and 'selfish DNA' and are found on plasmids and in the *E.coli* chromosome. Transposon structure is variable, but usually comprises recombinase genes flanked by repeated DNA sequences; the recombinase (s) together with host factors catalyse insertion of the transposon into sites on the chromosone, by a mechanism which usually results in a duplication of site at which the transposon has inserted. Insertion by some transposons can be highly site-specific whereas others insert essentially at random. For the purpose of transferring genes from one replicon to another, the donor gene could be incorporated within a highly site specific transposon such as Tn 7. The recipient plasmid would be engineered to contain the target DNA sequence.

One of the most fully understood site-specific recombination systems is that used in integration and excision of bacteriophage lambda (In *"Escherichia coli* and *Salmonella typhimurium*. Cellular and Molecular Biology." (1987). pp10654–1060. Neidhart, F. C. Editor in Chief. American Society for Microbiology). This bacteriophage can follow two developmental pathways once inside the cell: lysis or lysogeny. The lysogenic pathway involves integration of the lambda genome into the chromosome of the infected bacterium; integration is the result of a site-specific recombination between a ca. 240 bp sequence in the bacteriophage called att P and a 25 bp site in the bacterial chromosone called att B. The integration event is catalysed by a host encoded factor called IHF and a phage encoded enzyme called Int recombinase, which recognises a 15 bp region common to the two att sites. The integrated DNA is flanked by sequences derived from att B and att P, and these are called att L and att R. The integration event is reversible and is catalysed by Int, IHF and a second bacteriophage encoded enzyme, Xis. It is envisaged that this system could be used for sequence transfer between replicons within *E.coli*. For example, the donor gene could be flanked by att L and att R sites such that when Int and Xis proteins are provided in the host cell, recombination between att L and att R sites would create a circular DNA segment containing the donor gene and a recreated att B site. This circular segment could then recombine with an att P site engineered into the recipient plasmid.

Figure 3A:
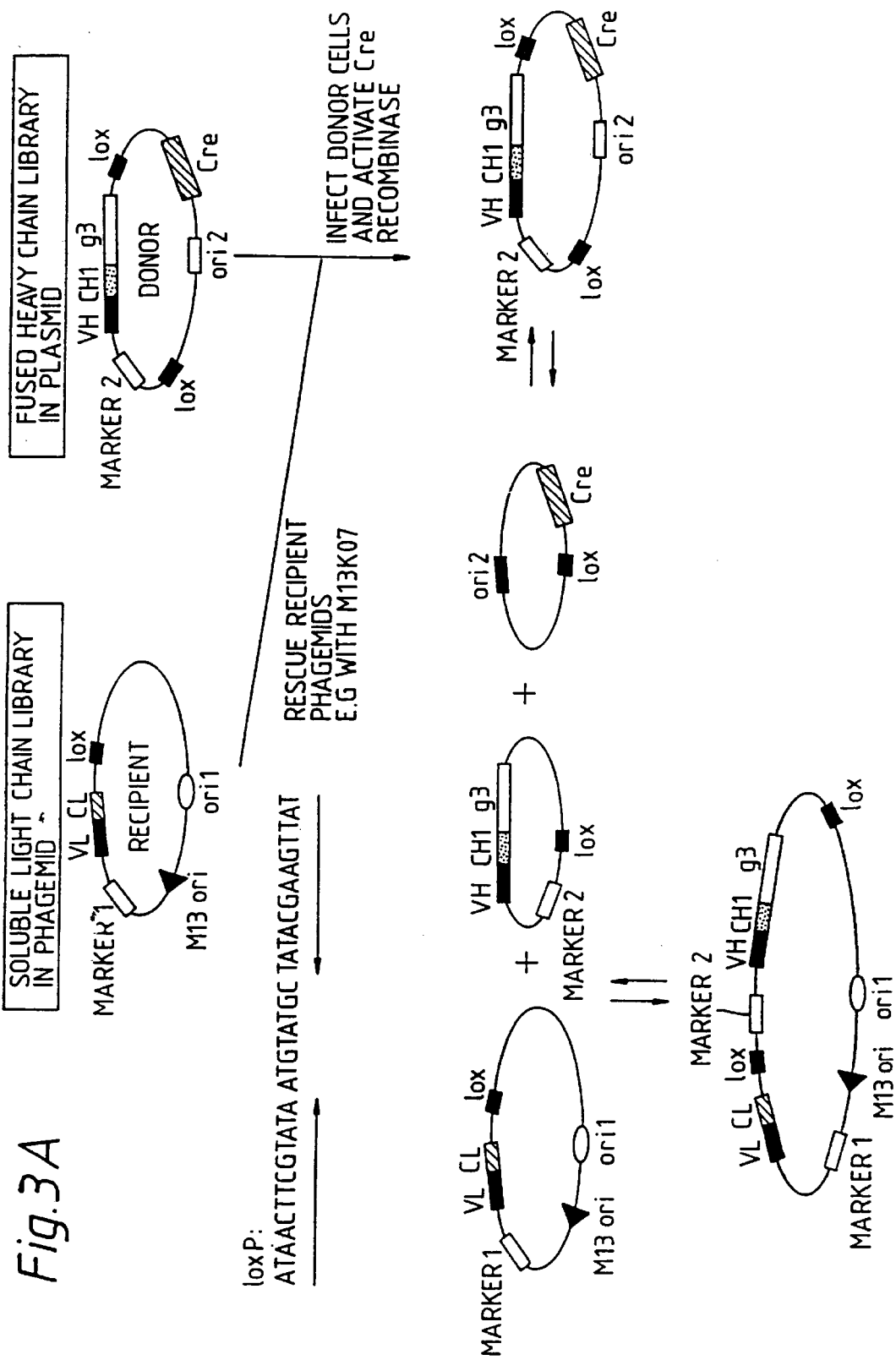
FIGS. 3A and 3B illustrate the use of sites specific recombination for construction of polycombinantorial libraries.
Figure 3B:
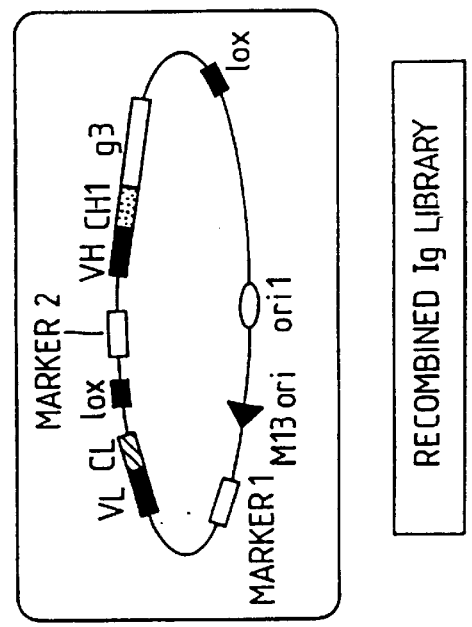
Figure 3B:
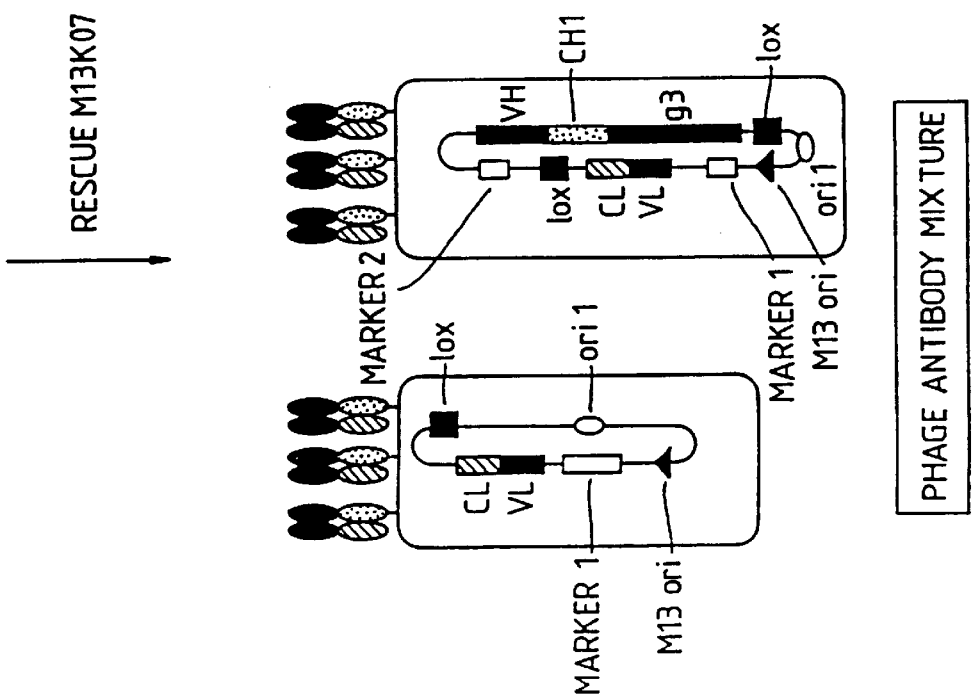

An alternative site specific recombination system is the lox P/Cre recombinase system of coliphage P1 (Hoess, R. H. and Abremski, K. (1990) The Cre-lox recombination system. In 'Nucleic acids and Molecular Biology.' Eckstein, F. and Lilley, D. M. J. eds. Vol 4, pp99–109, Springer-Verlag, Berlin, Heidelberg). Cre-recombinase catalyses a highly specific recombination event at sequences called lox. lox P, the recombination site in phage P1 consists of two 13 bp inverted repeats separated by an 8 bp non-symmetrical core (FIG. 3). For the work descended in this application, the lox P/Cre system was chosen of the alternatives available because the recombination is highly sequence-specific, very efficient and occurs at a short target site that is readily incorporated into cloning vectors.

In the example outlined configuration in FIG. 3 soluble light chain is cloned onto a phagemid containing a single lox P site. The heavy chains are cloned onto a plasmid as g3 fusions. Alongside the g3 fusion is the gene for a selectable marker, and the heavychain/g3/marker sequence flanked by two lox P sites. This plasmid also contains the Cre recombinase on a regulatable promoter and has an origin of double-stranded replication that is compatible with that on the phagemid in addition to that on the helper phage e.g. pl5A, RSF 1010 and col E1 origins will co-exist in the same cell. The phagemids are then infected into cells containing the donor plasmid and the Cre recombinase promoter induced, so that recombination between the lox P sites occurs inside infected cells. Some of these recombination events will lead to the heavychain/g3/marker sequences transferring as a block onto the phagemid at its single lox P site. Phagemids are then rescued with a helper phage such as M13KO7 (see WO92/01047)and the resulting phagemid particles either directly selected on antigen or infected into fresh host cells and grown with selection for the presence of both markers; one from the phagemid itself and the other from the heavychain/g3/marker block.

The use of site-specific recombination to bring genes onto the same replicon may be extended to creation of a continuous coding sequence on the same replicon, for example to construct single-chain Fv molecules. There is a single open reading frame in the loxP sequence that could be incorporated into an scFv linker which would then be a substrate for Cre-catalysed site-specific recombination. Placement of such modified scFv linker sequences at one or both ends of the genes to be fused can then result in creation of continuous open reading frames in vivo or in vitro when Cre recombinase is provided.

As with other site-specific recombination systems, Cre-catalysed recombination is reversible such that productive recombinants form only a fraction of the recombinants. Selection of productive rearrangements may be facilitated by use of a polA strain of bacteria, preferably *E.coli* or other gram negative bacterium. These cells are deficient in DNA polymerase I and are unable to support replication of plasmids (Johnston, S. and Ray, D. S. 1984, supra.). However, they are able to support replication of filamentous phage and plasmids containing filamentous phage intergenic regions. If Cre-catalysed recombination is performed in polA bacteria, by selecting for the presence of both selectable markers in the same pol A cell successful recombination events are enriched, since recombination must take place for the second marker gene to be replicated and expressed. The resulting cells then contain the complete repertoire and can be propagated as cells and infected with helper phage to produce phagemids containing the genes for both chains and expressing them on their surface.

Another way of enriching for productive recombination events is to employ mutant loxP sites. Several mutants of the loxP sequence are known, and these are compromised with respect to their ability to recombine with each other and the wild-type loxP sequence (Hoess, R. H., Wierzbicki, A. and Abremski, K. (1986) Nucl. Acids Res. 14, 2287–2300). For example, loxP 511 has a G→A point mutation in the central 8 bp segement, with the result that it will only recombine with other loxP 511 sites, but not the wild-type loxP sequence (Hoess, R. H., Wierzbicki, A. and Abremski, K. (1986) et supra.). Placement of wild-type and mutant loxP sequence combinations can direct which recombination events are possible: their use is described in example 1. Other mutant loxP sites are known but their abilities to recombine with each other and the wild-type loxP sequence have not been extensively characterised, presumably loxP 511 is not unique. Provision of different mutant loxP sites in the vectors would permit even greater control over the occurance of recombination events perhaps leading to more complex, controllable and efficient recombination strategies being possible.

The presence of target DNA sequences for site-specific recombination in the vectors has utility for subsequent manipulation of the genes. Naturally occurring or artificially introduced loxP sequences in the genomes of prokaryotic and eukaryotic organisms can be used as target sites for insertion of genes. Moreover, since Cre-catalysed recombination occurs readily in vitro, rapid and efficient transfer of genes in vitro, for example between different vectors, is also contemplated (Boyd, A. C. (1993) Nuc. Acids Res. 21, 817–821)

It will be apparent that the concept of using two or more replicons to generate diversity is not confined to display of multimers on the surface of filamentous bacteriophages. For example, bacteria could be used as the replicable genetic display package. For example, Fuchs et al. have shown that functional antibody can be displayed on the surface of *E.coli* by fusion to peptidoglycan-associated lipoprotein (Fuchs, P., Breitling, F., Dubel, S., Seehaus, T and Little, M. (1991) Targetting of recombinant antibodies to the surface of *Escherichia coli*: fusion to a peptidoglycan associated lipoprotein. BioTechnology 9, 1369–1373.). Klauser et al. describe transport of a heterologous protein to the surface of *E.coli* by fusion to Neisseria IgA protease (Klauser, T., Pohler, J. and Meyer, T. F. (1990) Extracellular transport of cholera toxin B subunit using Neisseria IgA protease B domain: conformation-dependent outer membrane translocation. EMBO 9, 1991–1999). Other surface proteins such as pili, ompA or the surface-exposed lipoprotein Tra T could also be used, and gram positive organisms such as lactobacilli and streptococci employed. Cloning and expression in Eukaryotic organisms is also contemplated.

Alternative cloning strategies are possible when cells are used in place of phage. For example, replicons can be introduced into the cells by conjugation, in addition to transformation and infection. Moreover, one or more genes can be recombined or transposed into the chromosome reducing the limitation of having to use compatible replicons.

The polycombinatorial concept is also particularly advantageous for mutagenesis experiments by allowing far greater numbers of mutant progeny to be produced. For example, if the genes encoding a multimeric peptide or polypeptide are mutated at a total of 10 amino acid positions, to incorporate any amino acid at these positions, then the total number of combinations is $20^{10}=>1.024 \ 10^{13}$. This figure is way beyond the reach of standard cloning formats, but can be achieved using the approaches described here.

The methods described here are applicable to multimeric proteins other than antibodies, such a T cell receptors, CD3 and insulin receptor. Libraries of proteins having more than two different and diverse subunits can be created by, for example, more than one cycle of infection. Cells containing one of the subunits are infected with phage containing the second subunit and the resulting population infected a second time with a compatible phage carrying the third subunit.

In some cases, it is advantageous to express all components of the multimer as g3 fusions. This will have the benefit stabilising weak interactions between seperate chains, e.g. VHg3 and VLg3 to create phage or phagemid particles with both VH and VL fused to g3 on the same particle, or stabilising polypeptides which interact weakly, or polypeptides which only associate in the presence of ligand.

The numbers of combinations possible with the polycombinatorial approach is limited only by the number of clones present in each of the repertoires, and, in the specific instance of using phage supplying one chain to infect cells containing the other, by the numbers of phage and cells that can be produced. The use of more sophisticated methods, for example fermentation technology, will allow even greater numbers of combinations to be accessed.

The nucleic acid encoding first and second polypeptide components of antibodies may be derived from the repertoire of an immunised or unimmunised animal or human, or from an artificially rearranged immunoglobulin gene or genes. Artificial rearrangement of immunoglobulin genes may involve joining of germ-line V segments in vitro to J segments and, in the case of VH domains, D segments. Any of the V, D and J segments may be synthetic. The joining may use a PCR-based process which may use primers which have a region of random sequence to introduce sequence diversity into the product, artificially rearranged immunoglobulin genes.

Filamentous F-specific bacteriophages are suitable examples of the type of phage which provide a vehicle for the display of binding molecules e.g. antibodies and antibody fragments and derivatives thereof, on their surface and facilitate subsequent selection and manipulation.

The F-specific phages (e.g. fl, fd and M13) have evolved a method of propagation which does not kill the host cell and they are used commonly as vehicles for recombinant DNA (Kornberg, A., DNA Replication, W. H. Freeman and Co., San Francisco, 1980). Gene III of phage fd is attractive for the insertion of biologically active foreign sequences. There are however, other candidate sites including for example gene VIII and gene VI.

The protein encoded by gene III has several domains (Pratt, D., et al., 1969 Virology 39:42–53., Grant, R. A., et al., 1981, J. Biol. Chem. 256: 539–546 and Armstrong, J., et al., FEBS Lett. 135: 167–172 1981).

The gene coding sequences for biologically active antibody fragments have been inserted into the gene III region of fd to express a large fusion protein. An initial vector used was fd-tet (Zacher, A. N., et al., 1980, Gene 9, 127–140) a tetracycline resistant version of fd bacteriophage that can be propagated as a plasmid that confers tetracycline resistance to the infected *E.coli* host. The applicants chose to insert after the signal sequence of the fd gene III protein for several reasons. In particular, the applicants chose to insert after amino acid 1 of the mature protein to retain the context for the signal peptidase cleavage. To retain the structure and function of gene III itself, the majority of the original amino acids are synthesized after the inserted immunoglobulin sequences. The inserted immunoglobulin sequences were designed to include residues from the switch region that links VH-VL to CH1-CL (Lesk, A., and Chothia, C., Nature 335, 188–190, 1988).

By manipulating gene III of bacteriophage fd, one can construct a bacteriophage that displays on its surface large biologically functional antibody, enzyme, and receptor molecules whilst remaining intact and infectious. Furthermore, the phages bearing antibodies of desired specificity, can be selected from a background of phages not showing this specificity.

The sequences coding for a population of antibody molecules and for insertion into the vector to give expression of antibody binding functions on the phage surface can be derived from a variety of sources. For example, immunised or non-immunised rodents or humans, and from organs such as spleen and peripheral blood lymphocytes. The coding sequences are derived from these sources by techniques familiar to those skilled in the art (Orlandi, R., et al., 1989 supra; Larrick, J. W., et al., 1989 supra; Chiang, Y. L., et al., 1989 Bio Techniques 7, p. 360–366; Ward, E. S, et al., 1989 supra; Sastry, L., et al., 1989 supra.)

In standard recombinant techniques for the production of antibodies, an expression vector containing sequences coding for the antibody polypeptide chains is used to transform e.g. E.coli. The antibody polypeptides are expressed and detected by use of standard screening systems. When the screen detects an antibody polypeptide of the desired specificity, one has to return to the particular transformed E.coli expressing the desired antibody polypeptide. Furthermore, the vector containing the coding sequence for the desired antibody polypeptide then has to be isolated for use from E.coli in further processing steps.

In the present invention however, the desired antibody polypeptide when expressed, is already packaged with its gene coding sequence. This means that when the an antibody polypeptide of desired specificity is selected, there is no need to return to the original culture for isolation of that sequence. Furthermore, in previous methods in standard recombinant techniques, each clone expressing antibody needs to be screened individually. The present application provides for the selection of clones expressing antibodies with desired properties.

Because a rgdp (eg a pAb) displays a member of a specific binding pair (eg. an antibody of monoclonal antigen-binding specificity) at the surface of a relatively simple replicable structure also containing the genetic information encoding the member, rgdps eg pAbs, that bind to the complementary member of the specific binding pair (eg antigen) can be recovered very efficiently by either eluting off the complementary member using for example diethylamine, high salt etc and infecting suitable bacteria, or by denaturing the structure, and specifically amplifying the sequences encoding the member using PCR. That is, there is no necessity to refer back to the original bacterial clone that gave rise to the pAb.

SELECTION FORMATS AND AFFINITY MATURATION

Individual rgdps eg pAbs expressing the desired specificity eg for an antigen, can be isolated from the complex library using the conventional screening techniques (e.g. as described in Harlow, E., and Lane, D., 1988, supra Gherardi, E et al. 1990. J. Immunol. meth. 126 p61–68).

Other selection techniques, described and illustrated in WO 92/01047, are practicable only because of the unique properties of rgdps. The general outline of some screening procedures is illustrated in FIG. 5 using pAbs as an example type of rgdp.

The population/library of pAbs to be screened could be generated from immunised or other animals; or be created in vitro by mutagenising pre-existing phage antibodies (using techniques well-known in the art such as oligonucleotide directed mutagenesis (Sambrook, J., et al., 1989 Molecular Cloning a Laboratory Manual, Cold Spring Harbor Laboratory Press). This population can be screened in one or more of the formats described below with reference to FIG. 5, to derive those individual pAbs whose antigen binding properties are different from sample c.

Binding Elution

Figure 5A:
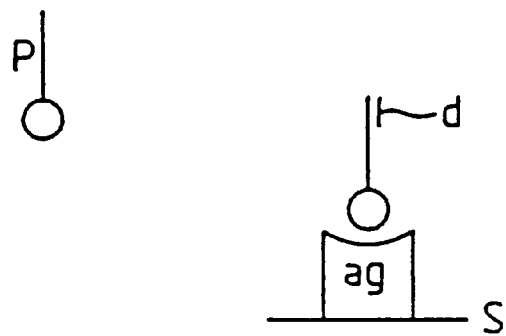
FIGS. 5-FIG. 5B show schematically selection techniques which utilise the unique properties of pAbs; 5(A) shows a binding/elution system; and 5(B) shows a competition system (p=pAb; ag=antigen to which binding by pAb is required; c=competitor population e.g. antibody, pAb, ligands; s=substrate (e.g. plastic beads etc); d=detection system.
Figure 5B:
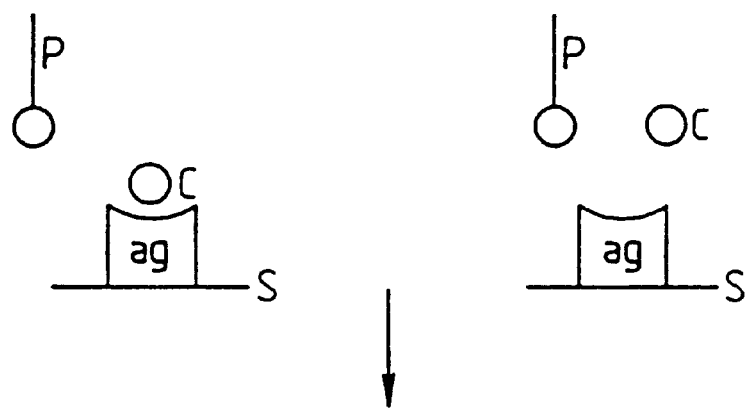
Figure 5B:

FIG. 5(i) shows antigen (ag) bound to a solid surface (s) the solid surface (s) may be provided by a petri dish, chromatography beads, magnetic beads and the like. The population/library of pAbs is then passed over the ag, and those individuals p that bind are retained after washing, and optionally detected with detection system d. A detection system based upon anti-fd antisera is illustrated in more detail in example 4 of WO 92/01047. If samples of bound population p are removed under increasingly stringent conditions, the binding affinity represented in each sample will increase. Conditions of increased stringency can be obtained, for example, by increasing the time of soaking or changing the pH of the soak solution, etc.

Competition

Referring to FIG. 5(ii) antigen ag can be bound to a solid support s and bound to saturation by the original binding molecule c. If a population of mutant pAb (or a set of unrelated pAbs) is offered to the complex, only those that have higher affinity for antigen ag than c will bind. In most examples, only a minority of population c will be displaced by individuals from population p. If c is a traditional antibody molecule, all bound material can be recovered and bound p recovered by infecting suitable bacteria and/or by use of standard techniques such as PCR.

An advantageous application is where ag is used as a receptor and c the corresponding ligand. The recovered bound population p is then related structurally to the receptor binding site/and or ligand. This type of specificity is known to be very useful in the pharmaceutical industry.

Another advantageous application is where ag is an antibody and c its antigen. The recovered bound population p is then an anti-idiotype antibody which have numerous uses in research and the diagnostic and pharmaceutical industries.

At present it is difficult to select directly for anti-idiotype antibodies. pAbs would give the ability to do this directly by binding pAb libraries (eg a naive library) to B cells (which express antibodies on their surface) and isolating those phage that bound well.

In some instances it may prove advantageous to pre-select population p. For example, in the anti-idiotype example above, p can be absorbed against a related antibody that does not bind the antigen.

However, if c is a pAb, then either or both c and p can advantageously be marked in some way to both distinguish and select for bound p over bound c. This marking can be physical, for example, by pre-labelling p with biotin; or more advantageously, genetic. For example, c can be marked with an EcoB restriction site, whilst p can be marked with an EcoK restriction site (see Carter, P. et al., 1985, Nucl. Acids Res. 13, 4431–4443). When bound p+c are eluted from the antigen and used to infect suitable bacteria, there is restriction (and thus no growth) of population c (i.e. EcoB restricting bacteria in this example). Any phage that grew, would be greatly enriched for those individuals from p with higher binding affinities. Alternatively, the genetic marking can be achieved by marking p with new sequences, which can be used to specifically amplify p from the mixture using PCR.

Since the bound pAbs can be amplified using for example PCR or bacterial infection, it is also possible to rescue the desired specificity even when insufficient individuals are bound to allow detection via conventional techniques.

The preferred method for selection of a phage displaying a protein molecule with a desired specificity or affinity will often be elution from an affinity matrix with a ligand (eg example 21 of WO 92/01047). Elution with increasing concentrations of ligand should elute phage displaying binding molecules of increasing affinity. However, when eg a pAb binds to its antigen with high affinity or avidity (or another protein to its binding partner) it may not be possible to elute the pAb from an affinity matrix with molecule related to the antigen. Alternatively, there may be no suitable specific eluting molecule that can be prepared in sufficiently high concentration. In these cases it is necessary to use an elution method which is not specific to eg the antigen-antibody complex. Some of the nonspecific elution methods generally used reduce phage viability for instance, phage viability is reduced with time at pH12 (Rossomando, E. F. and Zinder N. D. J. Mol.Biol. 36 387–399 1968). There may be interactions between eg antibodies and affinity matrices which cannot be disrupted without completely removing phage infectivity. In these cases a method is required to elute phage which does not rely on disruption of eg the antibody—antigen interaction. A method was therefore devised which allows elution of bound pAbs under mild conditions (reduction of a dithiol group with dithiothreitol) which do not disrupt phage structure (example 47 of WO 92/01047).

This elution procedure is just one example of an elution procedure under mild conditions. A particularly advantageous method would be to introduce a nucleotide sequence encoding amino acids constituting a recognition site for cleavage by a highly specific protease between the foreign gene inserted, in this instance a gene for an antibody fragment, and the sequence of the remainder of gene III. Examples of such highly specific proteases are Factor X and thrombin. After binding of the phage to an affinity matrix and elution to remove non-specific binding phage and weak binding phage, the strongly bound phage would be removed by washing the column with protease under conditions suitable for digestion at the cleavage site. This would cleave the antibody fragment from the phage particle eluting the phage. These phage would be expected to be infective, since the only protease site should be the one specifically introduced. Strongly binding phage could then be recovered by infecting eg. *E.coli* TG1 cells.

An alternative procedure to the above is to take the affinity matrix which has retained the strongly bound pAb and extract the DNA, for example by boiling in SDS solution. Extracted DNA can then be used to directly transform *E.coli* host cells or alternatively the antibody encoding sequences can be amplified, for example using PCR with suitable primers such as those disclosed herein, and then inserted into a vector for expression as a soluble antibody for further study or a pAb for further rounds of selection.

Another preferred method for selection according to affinity would be by binding to an affinity matrix containing low amounts of ligand.

If one wishes to select from a population of phages displaying a protein molecule with a high affinity for its ligand, a preferred strategy is to bind a population of phage to an affinity matrix which contains a low amount of ligand.

There is competition between phage, displaying high affinity and low affinity proteins, for binding to the ligand on the matrix. Phage displaying high affinity protein is preferentially bound and low affinity protein is washed away. The high affinity protein is then recovered by elution with the ligand or by other procedures which elute the phage from the affinity matrix (example 35 of WO 92/01047 demonstrates this procedure).

In summary then, for recovery of the packaged DNA from the affinity step, the package can be simply eluted, it can be eluted in the presence of a homologous sbp member which competes with said package for binding to a complementary sbp member; it could be removed by boiling, it could be removed by proteolytic cleavage of the protein; and other methods will be apparent to those skilled in the art eg. destroying the link between the substrate and complementary sbp member to release said packaged DNA and sbp member. At any rate, the objective is to obtain the DNA from the package so that it can be used directly or indirectly, to express the sbp member encoded thereby.

The efficiency of this selection procedure for pAbs and the ability to create very large libraries means that the immunisation techniques developed to increase the proportion of screened cells producing antibodies of interest will not be an absolute requirement. The technique allows the rapid isolation of binding specificities eg antigen-binding specificities, including those that would be difficult or even unobtainable by conventional techniques, for example, catalytic or anti-idiotypic antibodies. Removal of the animal altogether is now possible, once a complete library of the immune repertoire has been constructed.

The structure of the pAb molecule can be used in a number of other applications, some examples of which are:

Signal Amplification

Acting as a molecular entity in itself, rgdps eg pAbs combine the ability to bind a specific molecule eg antigen with amplification, if the major coat protein is used to attach another moiety. This moiety can be attached via immunological, chemical, or any other means and can be used, for example, to label the complex with detection reagents or cytotoxic molecules for use in vivo or in vitro.

Physical Detection

The size of the rgdps eg pAbs can be used as a marker particularly with respect to physical methods of detection such as electron microscopy and/or some biosensors, e.g. surface plasmon resonance.

Diagnostic Assays

The rgdps eg pAbs also have advantageous uses in diagnostic assays, particularly where separation can be effected using their physical properties for example centrifugation, filtration etc.

EXAMPLE 1

In vivo recombination of antibody genes between replicons using Cre/lox

This example illustrates using the Cre/loxP system to transfer antibody genes between two replicons in the same cell. Here, recombination must occur to produce a functional pairing of antibody genes.

Figure 4A:
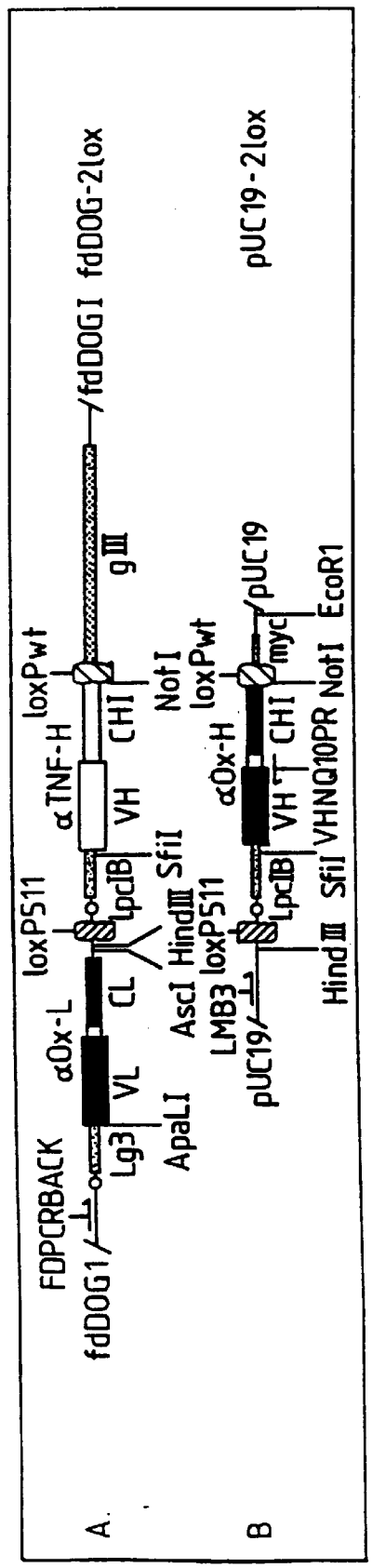
Figures 1, 4A:
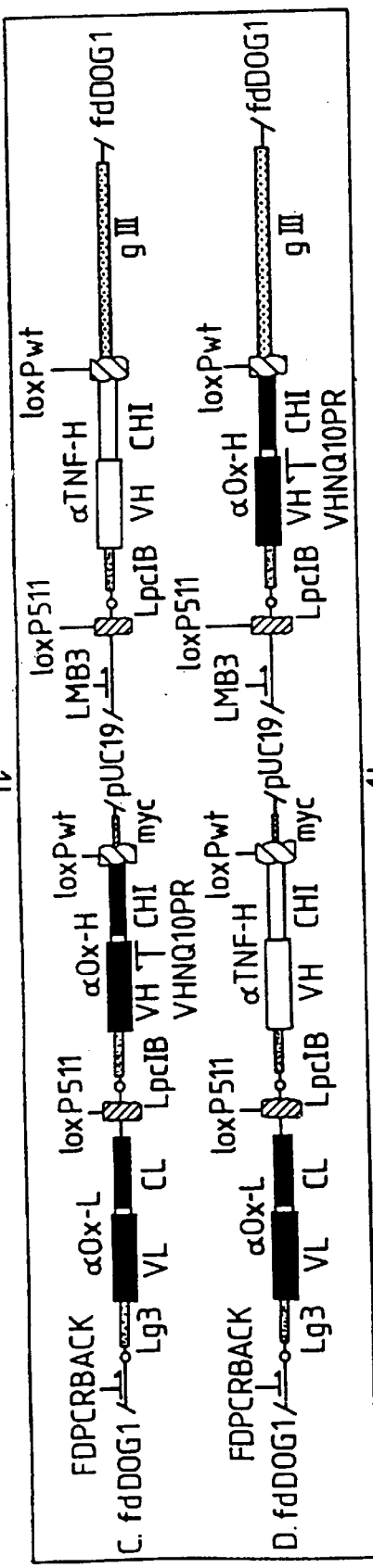

Two constructs were made: an "acceptor" fd phage vector, fdDOG-2lox (A) and a "donor" plasmid vector, pUC19–2lox (B) (see FIG. 4. and legend). A encodes the light chain of a first antibody (and the heavy chain from a second, different antibody): B encodes the heavy chain of the first antibody. In both vectors the VH genes are flanked by two loxP sites (see FIG. 4.). To avoid deletion of the VH genes in the presence of Cre, one of the loxP sites is wild-type but the other contains a G to A point mutation within the 8 bp spacer region loxP 511 (Hoess, R. H., Wierzbicki, A. and Abremski, K. (1986) et supra.). The wild-type loxP site and the mutant loxP 511 site do not recombine with each other in the same vector, but will, as shown below, recombine with sites of matching sequence in different vectors. When Cre recombinase is provided in vivo by infecting the E. coli with phage PlCm cl.100 (Rosner, J. L. (1972) Virology, 48, 679–689), A and B can co-integrate by recombination between either mutant or wild-type loxP sites to create chimaeric plasmids C or D respectively. Further recombination can then occur between the two wild-type or the two mutant loxP sites, to generate the original vectors (A and B) or two new vectors (E and F). The heavy chains of A and B are therefore exchanged, and E now encodes the Fab fragment of the first antibody for display as a fusion to the N-terminus of the phage gene 3 protein (g3p).

(a) Construction of fdDOG-2lox and pUC19-2lox Vectors.

FdDOG-2lox and pUC19-2lox vectors were derived from fdDOG-1 and pUC19 respectively (WO 92/01047 and WO 92/20791; fdDOG-1 previously called fdCAT-2). The cloning sites of these vectors were engineered using a combination of site-directed mutagenesis and ligation of double-stranded synthetic oligonucleotides using standard molecular biology techniques (Sambrook, J., Fritsch, E. F. and Maniatis, T. (1990) "Molecular cloning-a laboratory manual". Cold Spring Harbor Laboratory, New York.).

These constructs were used to produce donor plasmid B and acceptor phage A depicted in FIG. 4. Plasmid B contains the VH gene of the anti-phox (2-phenyloxazol-5-one) hybridoma NQ10.12.5 (Griffiths, G. M., Berek, C., Kaartinen, M. and Milstein, C. (1984) Nature, 312, 271–275.) linked to a human Cg1 segment, and cloned into pUC19-2lox as an Sfi 1-Not 1 fragment. Acceptor phage A contains the VL partner of the anti-phOx hybridoma NQ10.12.5 linked to a human Ck1 segment cloned into fdDOG-2lox as an Apa LI-Asc I fragment. Acceptor phage A also contains a VH segment from an anti-Tumour Necrosis Factor antibody (Rathjen, D. A., Furphy, L. J. and Aston, R. (1992) Br. J. Cancer, 65, 852–856.) linked to a human Cm1 segment, and cloned into fdDOG-2lox as an Sfi 1-Not 1 fragment.

Both A and B constructs were transformed into E.coli TG1, construct A conferring resistance to tetracyclin, construct B conferring resistance to ampicillin.

(b) Preparation of Infectious Acceptor Phase Particles (construct A).

Phage particles were harvested from the medium of construct B clones grown overnight in 2×YT containing tetracycline, as described in PCT WO 92/01047, example 6.

(c) In Vivo Cre-catalysed Recombination.

This was performed as follows:
1. E. coli containing the plasmid pUC19-2lox were grown, shaking at 37° C. in 2 ml 2×TY medium with 100 mg/ml ampicillin and 1% glucose to an O.D.600 nm of 0.4.
2. $5 \times 10^9$ transducing units (tu) fdDOG-2lox phage were added (a ten-fold excess over bacteria) and incubation continued at 37° C. without shaking for 30 min.
3. $5 \times 10^9$ pfu phage PlCm cl.100 (confer chloramphenicol resistance; Rosner, J. L. (1972) et. supra.) were added and incubation continued for a further 30 min. at 37° C. 40 ml of this culture were then added to 2 ml 2×TY, 100 mg/ml ampicillin, 12.5 mg/ml tetracycline, 12.5 mg/ml chloramphenicol, 1% glucose. The culture was shaken for 40 hours at 30° C.
4. About $10^{10}$ tu phage fd particles (including recombinant phage) were harvested from the culture supernatant by centrifuging out bacteria at 13000 g for 5 min. and passing the supernatant through a 0.45 mm sterile filter (Minisart, Sartorius).

In order to sample the recombined population, $10^3$ tu of the above fd particles were infected into fresh E.coli TG1 and plated on 2×TY agar containing 12.5 mg/ml tetracycline then incubated at 37° C. overnight. Ninety six well seperated colonies were transferred to a 96 well microtitre tray containing 100 ml/well 2×TY containing 12.5 mg/ml tetracycline and grown at 37° C. overnight. This plate was used as a master stock which was then screened by several techniques to identify which recombination events had occurred:

(1) ELISA, to identify clones producing phage that bind to phOx-BSA (to identify vector E).
(2) Replica plating, to find clones resisitant to both ampicillin and tetracycline (to identify vectors C and D).
(3) Colony hybridisation, with a radiolabelled oligonucleotide VHNQ10PR (SEQ ID NO: 65) which binds specifically to CDR3 of NQ10.12.5 VH (to identify vectors C, D and E).
(4) PCR, with oligonucleotides FDPCRBACK (SEQ ID NO: 66) and VHNQ10PR (to identify vectors C and E).
(5) PCR, with oligonucleotides LMB3 (SEQ ID NO: 67) and VHNQ10PR (to identify vector D).

(d) ELISA to Identify phOX Binders (vector E)
1. Coat plate (Falcon 3912) with 100 µl of phOX-BSA (14:1 substitution) per well at 10 µg/ml, in PBS. Leave overnight at room temp.
2. Rinse wells 3×with PBS, and block with 200 µl per well of 2% Marvel/PBS, for 2 hs at 37° C.
3. Rinse wells 3×with PBS, then add 25 µl 10% Marvel/PBS to all wells.
4. Add 100 µl culture supernatant to the appropriate wells. Mix, leave 2 hrs room temp.
5. Wash out wells 3 times with PBS, 0.05% Tween 20 and times with PBS. Add 100 ml sheep anti-M13 antiserum diluted 1:1000 in 2% Marvel/PBS into each well. Incubate at room temp. for 1.5 hrs.
6. Wash out wells with 3 times with PBS, 0.05% Tween 20 and 3 times with PBS. Pipette 100 µl of 1:5000 dilution of anti-sheep IgG antibody (peroxidase-conjugated, Sigma). Incubate at room temp. for 1.5 hrs.
7. Discard 2nd antibody, and wash wells 3 times with PBS, 0.05% Tween 20 and 3 times with PBS.
8. Add one 10 mg ABTS (2,2'-azino bis (3-ethylbenzthiazoline-6-sulphonic acid), diammonium salt) tablet to 20 ml 50 mM citrate buffer, pH4.5. (50 mM citrate buffer, pH4.5 is made by mixing equal volumes 50 mM trisodium citrate and 50 mM citric acid).
9. Add 20 µl 30% hydrogen peroxide to the above solution immediately before dispensing.
10. Add 100 µl of the above solution to each well. Leave room temp. 30 min.
11. Quench by adding 50 µl 3.2 mg/ml sodium fluoride. Read at 405 nm.

Note 1: 'Marvel' is dried milk powder. PBS is 5.84 g NaCl, 4.72 g $Na_2HPO_4$ and 2.64 g $NaH_2PO_4.2H2O$, pH 7.2, in 1 litre.

68 of the 96 clones were found to be positive in the ELISA (O.D. 405 nM>1.0); 71% of the tetracycline resistant clones therefore correspond to vector E (fig.) since they encode functional anti-phOX Fab fragments on phage.

(e) Replica Plating to Identify Vectors C and D.

Cells from the master plate were inoculated onto a 2×YT agar plate containing 100 mg/ml ampicillin, 12.5 mg/ml tetracycline and 1% glucose, using a 96 pin device. The plate was incubated at 37° C. overnight. Five colonies had grown up the next day indicating that 5/96 clones had the structures shown in C or D.

(f) Colony Hybridisation to Identify Vectors C, D and E.

Colony hybridisation was performed with the array using standard techniques as described in Sambrook et al. (1989, supra.). The probe used was a radiolabelled oligonucleotide VHNQ10PR which binds specifically to CDR3 of NQ10.12.5 VH.

73 of the 96 colonies were positive and therefore correspond to vectors C, D or E.

(g) PCR Screening to Identify Vectors C and E.

PCR reactions were performed essentially as described in example 11, WO 92/01047. Cells from each of the 96 clones were carefully transferred using a toothpick into 20 ml sterile water in a 0.5 ml centrifuge tube. The samples were then placed in a boiling water bath for 5 minutes and 2 ml of this used as template for each 20 ml PCR reaction.

Thirty cycles of amplification were performed each of 94° C. 1 minute, 50° C. 1 minute and 72° C. 2 minutes, using primers FDPCRBACK and VHNQ1OPR. PCR reaction products were resolved on 1% TAE agarose gels (Sambrook et al. (1989) supra.).

72 of the 96 clones clones gave a ca. 1 Kb PCR fragment and were thus scored as positive. These clones correspond to vectors C and E.

(g) PCR Screening to Identify Vector D.

A second set of PCR reactions were performed on cells from the array as described above, this time using primers LMB3 and VHNQ10PR.

Only 1 of the 96 clones gave a ca. 400 bp PCR fragment and was thus scored as vector D.

(h) Analysis of Recombinants.

The preceding experiments show that of the 96 tetracycline resistant clones that were sampled, 23 were vector A, 4 vector C, 1 vector D and 68 vector E. All 68 vector E clones produced phage which bound to phOx-BSA, but the remaining 28 clones did not (as expected). Thus, 70% of all tetracycline resistant clones corresponded to vector E, which encodes functional anti-phOx Fabs for display on phage. The process is very efficient, and should allow the creation and use of extremely large combinatorial repertoires.

EXAMPLE 2

Creation of an Extremely Large Combinatorial Library using in Vivo Recombination.

This example describes construction of an extremely large library of V-genes from unimmunised donors, using the in vivo recombination strategy outlined in the previous example. Many of the procedures detailed below have been previously described (Marks, J et al. (1991) et supra.).

(a) Preparation of cDNA Template 500 ml of blood, containing approximately $10^8$ B-lymphocytes, was obtained from 2 healthy volunteers. The white cells were separated on Ficoll and RNA was prepared using a modified method (Cathala, G., J. Savouret, B. Mendez, B. L. Wesr, M. Karin, J. A. Martial and J. D. Baxter. (1983). A method for isolation of intact, transcriptionally active ribonucleic acid. DNA. 2, 329.). Three first strand CDNA syntheses were made as described by Marks et al (1991, supra.) from RNA corresponding to $2.5 \times 10^7$ B-cells, using HuIgMFOR (SEQ ID NO: 7) constant region primer for the heavy chains, and HUCKFORCYS (SEQ ID NO: 8) for kappa light chains and HuCLFORCYS (SEQ ID NO: 9) for lambda light chains (Table 1)

(b) PCR of Heavy Chains and Construction of Heavy Chain Repertoire.

VH genes were PCR-amplified using the HuIgMFOR primer in conjunction with each of the HuVHBACK primers (SEQ ID NOS: 10–15) individually. Six separate PCR amplifications were performed each of 50 µl reaction volume containing 5 µl of the supernatant from the cDNA synthesis using the HUIGMFOR primer, 20 pmol total concentration of the BACK primers, 20 pmol concentration of the FORWARD primer, 250 µM dNTPs, 10 mM KCl, 10 mM (NH4)2SO4, 20 mM Tris.HCl (pH 8.8), 2.0 mM MgCl2, 100 mg/ml BSA and 1 µl (1 unit) Vent DNA polymerase (New England Biolabs). The reaction mixture was overlaid with mineral (paraffin) oil and subjected to 30 cycles of amplification using a Techne PHC-2 thermal cycler. The cycle was 94° C. for 1 minute (denaturation), 57° C. for 1 minute (annealing) and 72° C. for 2.5 minutes (extension). The products were purified on a 1.0% agarose gel, isolated from the gel by Geneclean (Bio-101) and resuspended in 25 µlof $H_2O$. The six products were then pooled and 'pullthrough' PCR reactions performed to attach Sfi I and Not I restriction sites.

Pullthrough reactions were set up with the primers HUVHBACKSfi (equimolar mix of all 6 primers SEQ ID NOS: 16–21) and HUCMlFONO (SEQ ID NO: 22). 50 ml reactions of containing 5 µl of the pooled PCR products from the previous step were amplified using the same conditions as for the primary PCR except that 25 cycles of amplification were used. The resulting fragments were digested with Sfi I and Not I, gel-purified, and the fragments ligated to Sfi I and Not I cut pUC19-2lox using previously described procedures (Sambrook, J. et al. (1989) et supra; PCT WO 92/01047). The ligation mixes were phenol-chloroform extracted prior to electroporation into TG1 cells (Marks, J et al. (1991) et supra.). Briefly, the ligated DNA was resuspended in 20 µl of water, and 2.5 µl samples were electroporated into 50 µl aliquots of electro-competent E.coli TG1. Cells were grown in SOC for 1 hr and then plated on 2YT agar with 100 µg/ml ampicillin and 1% glucose (2YTAG) in 243×243 mm dishes (Nunc) then grown overnight at 30° C. Colonies were scraped off the plates into 2YTAG containing 15% glycerol for storage at −70° C. as library stocks.

The heavy chain repertoire was calculated to have ca. $1.10^7$ independent recombinants, which by Bst NI fingerprinting was shown to be extremely diverse (PCT WO 92/01047).

(c) PCR of Light Chains and Construction of Kappa and Lambda-chain Repertoires.

Kappa and lambda-chain genes were amplified separately. Kappa chain genes were amplified using an equimolar mixture of the 12 SYNKB primers (SEQ ID NOS: 23–24) in conjunction with HuCKFORCYS (SEQ ID NO: 8) (Table 1). 1-chain genes were amplified from the cDNA synthesis using an equimolar mix of the 8 DPVL primers (SEQ ID NOS: 48–55) in conjunction with the HUCLFORCYS primer (SEQ ID NO: 9). In each case 50 µl reaction mixtures were prepared containing 5 µl of the supernatant from the appropriate cDNA synthesis, 20 pmol total concentration of the BACK primers, 20 pmol concentration of the FORWARD primers, 250 µM dNTPs, 10 mM KCl, 10 mM (NH4)2SO4, 20 mM Tris.HCl (pH 8.8), 2.0 mM MgCl2, 100 mg/ml BSA and 1 µl (1 unit) Vent DNA polymerase (New England Biolabs). The reaction mixture was overlaid with mineral (paraffin) oil and subjected to 30 cycles of amplification using a Techne thermal cycler. The cycle was 94° C. for 1 minute (denaturation), 57° C. for 1 minute (annealing)

and 72° C. for 2.5 minutes (extension). The products were purified on a 1% agarose gel, isolated from the gel by Geneclean (Bio-101) and resuspended in 25 μl of H$_2$O.

Pullthrough reactions were now performed on each of the two light chain preparations. kappa-chain genes were amplified using an equimolar mixture of the 12 SYNKBApa primers (SEQ ID NOS: 35–46) in conjunction with either HUCKFORCYSNOT (SEQ ID NO: 47). lambda-chain genes were amplified using an equimolar mixture of the 8 DPVLApa primers (SEQ ID NOS: 56–63) in conjunction with HUCLFORCYSNOT (SEQ ID NO: 64). Pullthrough conditions were performed as for the primary light chain PCRs above except that 25 cycles of amplification were used.

Kappa and lambda-chain repertoires were processed seperately. In each case, PCR products were digested with Apa LI and Not I and ligated into Apa LI-Not I-cut fdDOG-2lox (prepared using the standard format), the ligation mixes were purified by phenol extraction and ethanol precipitated prior to electroporation into TG1 as above, except that transformed cells were plated on 2YT agar with 12.5 μg/ml tetracycline in 243×243 mm dishes (Nunc) then grown overnight at 30° C. Colonies were scraped off the plates into 2YT containing 15% glycerol for storage at −70° C. as library stocks.

The kappa and lambda-chain repertoires were calculated to have ca. $1.10^6$ independent recombinants; again, Bst NI fingerprinting indicates that both libraries were extremely diverse.

(d) In Vivo Recombination of Heavy and Light Chains.

The kappa and lambda-chain repertoires were seperately recombined with the heavy chain repertoire using a scale-up of the procedure described in example 1.

O.D.600 nm was used to calculate the cell density of the stocks scraped from the plates, using the algorithm O.D.600 nm of $1.0=5.10^8$ cells. Approximately $1.10^{10}$ cells from each of the kappa and lambda-chain repertoires in fdDOG-2lox were inoculated into 1 litre volumes of 2×YT containing 12.5 μg/ml tetracycline and grown for 30 hrs at 37 C with rapid shaking. Phage particles were harvested from the clarified growth medium as described in PCT WO 92/01047, example 6, and stocks adjusted to ca. $1.10^{12}$ TU ml-1.

$1.10^{11}$ cells from the heavy chain repertoire were inoculated into 2×1 litre volumes 2YTAG in 2.5 L shake flasks and grown at 37 C with rapid shaking until the cultures reached an O.D.$_{600nm}$ of 0.4 ml$^{-1}$. $5.10^{12}$ fdDOG-2lox kappa and lambda fdDOG-2lox phage were added (a ten-fold excess over bacteria) and incubation continued at 37° C. without shaking for 30 min. $5.10^{12}$ pfu phage P1Cm cl.100 were then added and incubation continued for a further 30 min. at 37° C. The cultures were then centrifuged at 4,000×g for 15 minutes at 4° C. and the supernatant poured off. The cell pellets were resuspended in llitre of 2×TY, 100 mg/ml ampicillin, 12.5 mg/ml tetracycline, 12.5 mg/ml chloramphenicol, 1% glucose and the cultures shaken for 40 hours at 30° C. Phage fd particles (including recombinant phage) were harvested from the culture supernatant by centrifuging out bacteria at 13000 g for 15 minutes and the particles PEG precipitated.

The recombined library phage were then resuspended in 10 mM TRIS-HCl (pH 8.0), lmM EDTA and adjusted to $1.10^{12}$ TU ml-1: this stock represents the library. These phage are selected on antigen, reinfected into fresh *E.coli* and recovered by plating on 2×YT agar containing 12.5 μg/ml tetracycline. Growth of selected phages is achieved by culture in 2×YT containing 12.5 μg/ml tetracycline (no other antibiotics necessary see FIG. 4, construct E), and phages bearing functional antibodies recovered from the growth medium.

Note: Sbp members and encoding nucleic acid therefor obtained using the present invention may be used in the production of derivatives. The term derivative is discussed above.

TABLE 1

Oligonucleotide sequences

ALL WRITTEN 5'->3'

A) Primers for first strand cDNA synthesis

Human IgM Constant Region Primer

HuIgMFOR    5'-TGG AAG AGG CAC GTT CTT TTC TTT-3'

Human kappa Constant Region Primer

HUCKFORCYS    5'-ACA CTC TCC CCT GTT GAA GCT CTT-3'

Human lambda Constant Region Primer

HUCLFORCYS    5'-TGA ACA TTC TGT AGG GGC CAC TGT CTT-3'

B) Heavy chain primary PCR

VH Primers

HuVH1aBACK    5'-CAG GTG CAG CTG GTG CAG TCT GG-3'
    HuVH2aBACK    5'-CAG GTC AAC TTA AGG GAG TCT GG-3'
    HuVH3aBACK    5'-GAG GTG CAG CTG GTG GAG TCT GG-3'
    HuVH4aBACK    5'-CAG GTG CAG CTG CAG GAG TCG GG-3'
    HuVH5aBACK    5'-GAG GTG CAG CTG TTG CAG TCT GC-3'
    HuVH6aBACK    5'-CAG GTA CAG CTG CAG CAG TCA GG-3'

Forward Primer

HuIgMFOR  5'-TGG AAG AGG CAC GTT CTT TTC TTT-3'

TABLE 1-continued

Oligonucleotide sequences

C) Heavy chain reamplification with restriction site primers

VH Back Primers

```
HuVH1aBACKSfi  5'-GTC CTC GCA ACT GCG GCC CAG CCG GCC
               ATG GCC CAG GTG CAG CTG GTG CAG
               TCT GG-3'
HuVH2aBACKSfi  5'-GTC CTC GCA ACT GCG GCC CAG CCG GCC
               ATG GCC CAG GTC AAC TTA AGG GAG
               TCT GG-3'
HuVH3aBACKSfi  5'-GTC CTC GCA ACT GCG GCC CAG CCG GCC
               ATG GCC GAG GTG CAG CTG GTG GAG
               TCT GG-3'
HuVH4aBACKSfi  5'-GTC CTC GCA ACT GCG GCC CAG CCG GCC
               ATG GCC CAG GTG CAG CTG CAG GAG
               TCG GG-3'
HuVH5aBACKSfi  5'-GTC CTC GCA ACT GCG GCC CAG CCG GCC
               ATG GCC CAG GTG CAG CTG TTG CAG
               TCT GC-3'
HuVH6aBACKSfi  5'-GTC CTC GCA ACT GCG GCC CAG CCG GCC
               ATG GCC CAG GTG CAG CTG TTG CAG
               TCA GG-3'
```

Forward primer

```
HCM1FONO  5'-CCA CGA TTC TGC GGC CGC CAC TGG AAG
          AGG CAC GTT CTT TTC TTT
```

D) Kappa chain primary PCR

Back primers

```
SYNKB1    5'-GAC ATC CAG (A/T)TG ACC CAG-3'
SYNKB2    5'-GTC ATC TGG ATG ACC CAG-3'
SYKKB3    5'-GCC ATC CAG ATG ACC CAG-3'
SYNKB4    5'-GAT (A/G)TT GTG ATG ACT CAG-3'
SYNKB5    5'-GA(T/G) ATT GTG ATG ACC CAG-3'
SYNKB6    5'-GAA ATT GTG TTG ACG CAG-3'
SYNKB7    5'-GAA ATA GTG ATG ACG CAG-3'
SYNKB8    5'-GAC ATC GTG ATG ACC CAG-3'
SYNKB9    5'-CAG CAG GGC AAT AAG CAC-3'
SYNKB10   5'-CAT CAG AGT AGT AGT TTA C-3'
SYNKB11   5'-AAC ATC CAG ATG ACC CAG-3'
SYNKB12   5'-GAA ATT GTA ATG ACA CAG-3'
```

Forward Primer

```
HUCKFORCYS          see above
```

E) Kappa chain reamplification with primers containing restriction sites

Back primers

```
SYNKB1APa  5'-CAT GAC CAC AGT GCA CTT GAC ATC CAG
           (A/T)TG ACC CAG-3'
SYNKB2Apa  5'-CAT GAC CAC AGT GCA CTT GTC ATC TGG ATG
           ACC CAG-3'
SYNKB3Apa  5'-CAT GAC CAC AGT GCA CTT GCC ATC CAG ATG
           ACC CAG-3'
SYNKB4Apa  5'-CAT GAC CAC AGT GCA CTT GAT (A/G)TT GTG
           ATG ACT CAG-3'
SYNKB5Apa  5'-CAT GAC CAC AGT GCA CTT GA(T/G) ATT GTG
           ATG ACC CAG-3'
SYNKB6Apa  5'-CAT GAC CAC AGT GCA CTT GAA ATT GTG TTG
           ACG CAG-3'
SYNKB7Apa  5'-CAT GAC CAC AGT GCA CTT GAA ATA GTG ATG
           ACG CAG-3'
SYNKB8Apa  5'-CAT GAC CAC AGT GCA CTT GAC ATC GTG ATG
           ACC CAG-3'
SYNKB9APa  5'-CAT GAC CAC AGT GCA CTT CAT CAG GGC AAT
           AAG CAC-3'
SYNKB10Apa 5'-CAT GAC CAC AGT GCA CTT CAT CAG AGT AGT
           AGT TTA C-3'
SYNKB11Apa 5'-CAT GAC CAC AGT GCA CTT AAC ATC CAG ATG
           ACC CAG-3'
```

TABLE 1-continued

Oligonucleotide sequences

SYNKB12Apa  5'-CAT GAC CAC AGT GCA CTT GAA ATT GTA ATG
                          ACA CAG-3'

Forward primers

HUCKFORCYSNOT  5'-GAG TCA TTC TCG ACT TGC GGC CGC ACA
                            CTC TCC CCT GTT GAA GCT CTT-3'

F) Lambda chain primary PCR

Back primers

DPVL1a     5'-CAG TCT GTG (T/C)TG ACG CAG CCG CC-3'
    DPVL1b     5'-CAG TCT GTC GTG ACG CAG CCG CC-3'
    DPVL1c     5'-CAG TCT GTG CTG ACT CAG CCA CC-3'
    DPVL2      5'-CA(G/A) TCT GCC CTG ACT CAG CCT-3'
    DPVL3a     5'-TCT TCT GAG CTG ACT CAG GAC CC-3'
    DPVL3b     5'-TCC TAT GAG CTG ACT CAG CCA CC-3'
    DPVL7/8    5'-CAG (A/G)CT GTG GTG AC(T/C) CAG GAG
                      CC-3'
    DPVL9      5'-C(A/T)G CCT GTG CTG ACT CAG CC(A/C)
                      CC-3'

Forward primer

HUCLFORCYS       see above

G) Lambda chain reamplification with primers containing restriction sites

Back primers

DPVL1aApa  5'-CAT GAC CAC AGT GCA CTT CAG TCT GTG
                   (T/C)TG ACG CAG CCG CC-3'
    DPVL1bApa  5'-CAT GAC CAC AGT GCA CTT CAG TCT GTC GTG
                   ACG CAG CCG CC-3'
    DPVL1cApa  5'-CAT GAC CAC AGT GCA CTT CAG TCT GTG CTG
                   ACT CAG CCA CC-3'
    DPVL2Apa   5'-CAT GAC CAC AGT GCA CTT CA(G/A) TCT GCC
                   CTG ACT CAG CCT-3'
    DPVL3aApa  5'-CAT GAC CAC AGT GCA CTT TCT TCT GAG CTG
                   ACT CAG GAC CC-3'
    DPVL3bApa  5'-CAT GAC CAC AGT GCA CTT TCC TAT GAG CTG
                   ACT CAG CCA CC-3'
    DPVL7/8Apa 5'-CAT GAC CAC AGT GCA CTT CAG (A/G)CT GTG
                   GTG AC(T/C) CAG GAG CC-3'
    DPVL9Apa   5'-CAT GAC CAC AGT GCA CTT C(A/T)G CCT GTG
                   CTG ACT CAG CC(A/C) CC-3'

Forward primers

HUCLFORCYSNOT  5'-GAG TCA TTC TCG ACT TGC GGC CGC TGA
                            ACA TTC TGT AGG GGC ACA TGT CTT-3'

H) Other primers/probes

VHNQ1OPR   5'-ATA AGC CCC GTA ATC TCT TGC-3
    FDPCRBACK  5'-GCB ATG GTT GTT GTC ATT GTC GGC-3
    LMB3       5'-CAG GAA ACA GCT ATG AC-3

---

What is claimed is:

1. A specific binding pair memberwhich is a single chain specific binding pair member comprising a first polypeptide chain component and a second polypeptide chain component and which is specific for a complementary specific binding pair member of interest, produced by a method having the following steps:

(a) introducing into prokaryotic host cells
  (i) first vectors comprising nucleic acid encoding a genetically diverse population of said first polypeptide chain component fused to a component of a secreted replicable genetic display package for display of said polypeptide chain components at the surface of replicable genetic display packages; and
  (ii) second vectors comprising nucleic acid encoding a genetically diverse population of said second polypeptide chain components;
  said first vectors being packaged in infectious replicable genetic display packages and their introduction into prokaryotic host cells being by infection into prokaryotic host cells harbouring said second vectors, or
  said second vectors being packaged in infectious replicable genetic display packages and their introduction into prokaryotic host cells being by infection into host cells harbouring said first vectors; and (b) causing or allowing recombination between said first and second vectors within said prokaryotic host cells, the recombination being promoted by inclusion in said first and second vectors of sequences at which site-specific recombination occurs, which sequences at which site-specific recombination occurs are derived from a loxP sequence, resulting in recombinant vectors each of which comprises nucleic acid encoding a said single chain specific binding pair member comprising a said first polypeptide chain component and a said second polypeptide chain component and an amino acid sequence encoded by a sequence provided by recombination between said sequences at which site-specific recombination occurs, and capable of being packaged into a replicable genetic display packages using said replicable genetic display package component;

(c) expressing said single chain specific binding pair members, producing replicable genetic display packages which display at their surface said single chain specific binding pair members and which each comprise nucleic acid encoding a said single chain specific binding pair member;

(d) selecting by binding with said complementary specific binding pair member of interest one or more single chain specific binding pair members specific for said complementary specific binding pair member of interest, each single chain specific binding pair member thus selected being associated in its respective replicable genetic display package with nucleic acid encoding that single chain specific binding pair member;

(e) obtaining nucleic acid encoding a single chain specific binding pair member from its replicable genetic display package displaying a specific binding pair member selected in step (d);

(f) producing, by expression of encoding nucleic acid in a recombinant host organism, a single chain specific binding pair member comprising a first polypeptide chain component and a second polypeptide chain component and an amino acid sequence encoded by a sequence provided by recombination between said sequences at which site-specific recombination occurs and specific for said complementary specific binding pair member of interest, which single chain specific binding pair comprises a first polypeptide chain component which is as encoded by nucleic acid encoding a said first polypeptide chain component of a specific binding pair member selected in step (d) or is a derivative thereof by way of addition, deletion, substitution or insertion of one or more amino acids or by linkage of another molecule, and a second polypeptide chain component which is as encoded by nucleic acid encoding a said second polypeptide chain component of a specific binding pair member selected in step (d) or is a derivative thereof by way of addition, deletion, substitution or insertion of one or more amino acids or by linkage of another molecule.

2. A specific binding pair member according to claim 1 comprising an antibody antigen binding domain.

3. A specific binding pair member according to claim 2 which comprises a single chain Fv molecule.

4. A specific binding pair member according to claim 1 wherein said replicable genetic display packages are secreted bacteriophage.

5. A specific binding pair member according to claim 2 wherein said replicable genetic display packages are secreted bacteriophage.

6. A specific binding pair member according to claim 3 wherein said replicable genetic display packages are secreted bacteriophage.

7. A specific binding pair member according to claim 1 wherein the recombination takes place in a bacterial host which replicates phages or phagemids preferentially over plasmids.

8. A specific binding pair member according to claim 7 wherein said bacterial host is a PolA strain of *E. coli* or of another gram-negative bacterium.

9. A specific binding pair member according to claim 2 wherein the recombination takes place in a bacterial host which replicates phages or phagemids preferentially over plasmids.

10. A specific binding pair member according to claim 9 wherein said bacterial host is a PolA strain of *E. coli* or of another gram-negative bacterium.

11. A specific binding pair member according to claim 3 wherein the recombination takes place in a bacterial host which replicates phages or phagemids preferentially over plasmids.

12. A specific binding pair member according to claim 11 wherein said bacterial host is a PolA strain of *E. coli* or of another gram-negative bacterium.

13. A specific binding pair member according to claim 4 wherein the recombination takes place in a bacterial host which replicates phages or phagemids preferentially over plasmids.

14. A specific binding pair member according to claim 13 wherein said bacterial host is a PolA strain of *E. coli* or of another gram-negative bacterium.

15. A specific binding pair member according to claim 5 wherein the recombination takes place in a bacterial host which replicates phages or phagemids preferentially over plasmids.

16. A specific binding pair member according to claim 15 wherein said bacterial host is a PolA strain of *E. coli* or of another gram-negative bacterium.

17. A specific binding pair member according to claim 6 wherein the recombination takes place in a bacterial host which replicates phages or phagemids preferentially over plasmids.

18. A specific binding pair member according to claim 17 wherein said bacterial host is a PolA strain of *E. coli* or of another gram-negative bacterium.

* * * * *

SEQUENCE LISTING (1) GENERAL INFORMATION:

(iii) NUMBER OF SEQUENCES: 67

(2) INFORMATION FOR SEQ ID NO:1:

(i) SEQUENCE CHARACTERISTICS:
      (A) LENGTH: 116 base pairs (B) TYPE: nucleic acid
            (C) STRANDEDNESS: double
            (D) TOPOLOGY: circular (xi) SEQUENCE DESCRIPTION: SEQ ID NO:1:

GGAGAGTGTT AATAAGGCGC GCCAAAGCTT CCTTAATATA ACTTCGTATA ATGTATACTA     60

TACGAAGTTA TTAGGTCGCA TGCAAATTCT ATTTCAAGGA GACAGTCATA ATGAAA       116

(2) INFORMATION FOR SEQ ID NO:2:

(i) SEQUENCE CHARACTERISTICS:
            (A) LENGTH: 116 base pairs
            (B) TYPE: nucleic acid
            (C) STRANDEDNESS: double
            (D) TOPOLOGY: circular (xi) SEQUENCE DESCRIPTION: SEQ ID NO:2:

AACAGCTATG ACCATGATTA CGCCAAGCTT CCTTAATATA ACTTCGTATA ATGTATACTA     60

TACGAAGTTA TTAGGTCGCA TGCAAATTCT ATTTCAAGGA GACAGTCATA ATGAAA       116

(2) INFORMATION FOR SEQ ID NO:3:

(i) SEQUENCE CHARACTERISTICS:
            (A) LENGTH: 118 base pairs
            (B) TYPE: nucleic acid
            (C) STRANDEDNESS: double
            (D) TOPOLOGY: circular (xi) SEQUENCE DESCRIPTION: SEQ ID NO:3:

AAAGAACGTG CCTCTTCCAG TGGCGGCCGC CCTTAATATA ACTTCGTATA ATGTATGCTA     60

TACGAAGTTA TTAGGTCTGG CCGCAGAAAC TGTTGAAAGT TGTTTAGCAA AACCTCAT    118

(2) INFORMATION FOR SEQ ID NO: 4:

(i) SEQUENCE CHARACTERISTICS:
            (A) LENGTH: 39 amino acids
            (B) TYPE: amino acid
            (C) STRANDEDNESS: single
            (D) TOPOLOGY: linear (xi) SEQUENCE DESCRIPTION: SEQ ID NO: 4:

Lys Asn Val Pro Leu Pro Val Ala Ala Ala Leu Asn Ile Thr Ser Tyr
1               5                   10                  15

Asn Val Cys Tyr Thr Lys Leu Leu Gly Leu Ala Ala Glu Thr Val Glu
                20                  25                  30

Ser Cys Leu Ala Lys Pro His
            35

(2) INFORMATION FOR SEQ ID NO: 5:

(i) SEQUENCE CHARACTERISTICS:
            (A) LENGTH: 118 base pairs
            (B) TYPE: nucleic acid
            (C) STRANDEDNESS: double
            (D) TOPOLOGY: circular (xi) SEQUENCE DESCRIPTION: SEQ ID NO: 5:

GAAAGTTGAC CCCAAATCTT CAGCGGCCGC CCTTAATATA ACTTCGTATA ATGTATGCTA     60

TACGAAGTTA TTAGGTCTGG CCGCAGAACA AAAACTCATC TCAGAAGAGG ATCTGAAT    118

(2) INFORMATION FOR SEQ ID NO: 6:

(i) SEQUENCE CHARACTERISTICS:

(A) LENGTH: 39 amino acids
           (B) TYPE: amino acid
           (C) STRANDEDNESS: single
           (D) TOPOLOGY: linear (xi) SEQUENCE DESCRIPTION: SEQ ID NO: 6:

Lys Val Asp Pro Lys Ser Ser Ala Ala Ala Leu Asn Ile Thr Ser Tyr
 1               5                  10                  15

Asn Val Cys Tyr Thr Lys Leu Leu Gly Leu Ala Ala Glu Gln Lys Leu
            20                  25                  30

Ile Ser Glu Glu Asp Leu Asn
        35

(2) INFORMATION FOR SEQ ID NO: 7:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (xi) SEQUENCE DESCRIPTION: SEQ ID NO: 7:

TGGAAGAGGC ACGTTCTTTT CTTT                                    24

(2) INFORMATION FOR SEQ ID NO: 8:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (xi) SEQUENCE DESCRIPTION: SEQ ID NO: 8:

ACACTCTCCC CTGTTGAAGC TCTT                                    24

(2) INFORMATION FOR SEQ ID NO: 9:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (xi) SEQUENCE DESCRIPTION: SEQ ID NO: 9:

TGAACATTCT GTAGGGGCCA CTGTCTT                                 27

(2) INFORMATION FOR SEQ ID NO:10:

(i) SEQUENCE CHARACTERISTICS:
           (A) LENGTH: 23 base pairs
           (B) TYPE: nucleic acid
           (C) STRANDEDNESS: single
           (D) TOPOLOGY: linear (xi) SEQUENCE DESCRIPTION: SEQ ID NO:10:

CAGGTGCAGC TGGTGCAGTC TGG                                     23

(2) INFORMATION FOR SEQ ID NO:11:

(i) SEQUENCE CHARACTERISTICS:
           (A) LENGTH: 23 base pairs
           (B) TYPE: nucleic acid
           (C) STRANDEDNESS: single
           (D) TOPOLOGY: linear (xi) SEQUENCE DESCRIPTION: SEQ ID NO:11:

```
CAGGTCAACT TAAGGGAGTC TGG                                                     23

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:12:

GAGGTGCAGC TGGTGGAGTC TGG                                                     23

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:13:

CAGGTGCAGC TGCAGGAGTC GGG                                                     23

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:14:

GAGGTGCAGC TGTTGCAGTC TGC                                                     23

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:15:

CAGGTACAGC TGCAGCAGTC AGG                                                     23

(2) INFORMATION FOR SEQ ID NO:16:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:16:

GTCCTCGCAA CTGCGGCCCA GCCGGCCATG GCCCAGGTGC AGCTGGTGCA GTCTGG               56

(2) INFORMATION FOR SEQ ID NO:17:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:17:

GTCCTCGCAA CTGCGGCCCA GCCGGCCATG GCCCAGGTCA ACTTAAGGGA GTCTGG               56
```

(2) INFORMATION FOR SEQ ID NO:18:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:18:

GTCCTCGCAA CTGCGGCCCA GCCGGCCATG GCCGAGGTGC AGCTGGTGGA GTCTGG      56

(2) INFORMATION FOR SEQ ID NO:19:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:19:

GTCCTCGCAA CTGCGGCCCA GCCGGCCATG GCCCAGGTGC AGCTGCAGGA GTCGGG      56

(2) INFORMATION FOR SEQ ID NO:20:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:20:

GTCCTCGCAA CTGCGGCCCA GCCGGCCATG GCCCAGGTGC AGCTGTTGCA GTCTGC      56

(2) INFORMATION FOR SEQ ID NO:21:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:21:

GTCCTCGCAA CTGCGGCCCA GCCGGCCATG GCCCAGGTAC AGCTGCAGCA GTCAGG      56

(2) INFORMATION FOR SEQ ID NO:22:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:22:

CCACGATTCT GCGGCCGCCA CTGGAAGAGG CACGTTCTTT TCTTT      45

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:23:

GACATCCAGW TGACCCAG      18

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:24:

GTCATCTGGA TGACCCAG                                                           18

(2) INFORMATION FOR SEQ ID NO:25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:25:

GCCATCCAGA TGACCCAG                                                           18

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:26:

GATRTTGTGA TGACTCAG                                                           18

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:27:

GAKATTGTGA TGACCCAG                                                           18

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:28:

GAAATTGTGT TGACGCAG                                                           18

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:29:

GAAATAGTGA TGACGCAG                                                           18

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:30:

GACATCGTGA TGACCCAG                                                       18

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:31:

CAGCAGGGCA ATAAGCAC                                                       18

(2) INFORMATION FOR SEQ ID NO:32:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:32:

CATCAGAGTA GTAGTTTAC                                                   19

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:33:

AACATCCAGA TGACCCAG                                                     18

(2) INFORMATION FOR SEQ ID NO:34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:34:

GAAATTGTAA TGACACAG                                                     18

(2) INFORMATION FOR SEQ ID NO:35:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:35:

CATGACCACA GTGCACTTGA CATCCAGWTG ACCCAG                           36

(2) INFORMATION FOR SEQ ID NO:36:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:36:

CATGACCACA GTGCACTTGT CATCTGGATG ACCCAG                                     36

(2) INFORMATION FOR SEQ ID NO:37:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:37:

CATGACCACA GTGCACTTGC CATCCAGATG ACCCAG                                     36

(2) INFORMATION FOR SEQ ID NO:38:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:38:

CATGACCACA GTGCACTTGA TRTTGTGATG ACTCAG                                     36

(2) INFORMATION FOR SEQ ID NO:39:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:39:

CATGACCACA GTGCACTTGA KATTGTGATG ACCCAG                                     36

(2) INFORMATION FOR SEQ ID NO:40:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:40:

CATGACCACA GTGCACTTGA AATTGTGTTG ACGCAG                                     36

(2) INFORMATION FOR SEQ ID NO:41:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:41:

CATGACCACA GTGCACTTGA AATAGTGATG ACGCAG                                     36

(2) INFORMATION FOR SEQ ID NO:42:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:42:

CATGACCACA GTGCACTTGA CATCGTGATG ACCCAG                              36

(2) INFORMATION FOR SEQ ID NO:43:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:43:

CATGACCACA GTGCACTTCA GCAGGGCAAT AAGCAC                              36

(2) INFORMATION FOR SEQ ID NO:44:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:44:

CATGACCACA GTGCACTTCA TCAGAGTAGT AGTTTAC                             37

(2) INFORMATION FOR SEQ ID NO:45:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:45:

CATGACCACA GTGCACTTAA CATCCAGATG ACCCAG                              36

(2) INFORMATION FOR SEQ ID NO:46:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:46:

CATGACCACA GTGCACTTGA AATTGTAATG ACACAG                              36

(2) INFORMATION FOR SEQ ID NO:47:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:47:

GAGTCATTCT CGACTTGCGG CCGCACACTC TCCCCTGTTG AAGCTCTT                 48

(2) INFORMATION FOR SEQ ID NO:48:

(i) SEQUENCE CHARACTERISTICS:

```
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:48:

CAGTCTGTGY TGACGCAGCC GCC                                              23

(2) INFORMATION FOR SEQ ID NO:49:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:49:

CAGTCTGTCG TGACGCAGCC GCC                                              23

(2) INFORMATION FOR SEQ ID NO:50:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:50:

CAGTCTGTGC TGACTCAGCC ACC                                              23

(2) INFORMATION FOR SEQ ID NO:51:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:51:

CARTCTGCCC TGACTCAGCC T                                                21

(2) INFORMATION FOR SEQ ID NO:52:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:52:

TCTTCTGAGC TGACTCAGGA CCC                                              23

(2) INFORMATION FOR SEQ ID NO:53:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:53:

TCCTATGAGC TGACTCAGCC ACC                                              23

(2) INFORMATION FOR SEQ ID NO:54:

(i) SEQUENCE CHARACTERISTICS:
        (A) LENGTH: 23 base pairs
```

(B) TYPE: nucleic acid
            (C) STRANDEDNESS: single
            (D) TOPOLOGY: linear (xi) SEQUENCE DESCRIPTION: SEQ ID NO:54:

CAGRCTGTGG TGACYCAGGA GCC                                              23

(2) INFORMATION FOR SEQ ID NO:55:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:55:

CWGCCTGTGC TGACTCAGCC MCC                                              23

(2) INFORMATION FOR SEQ ID NO:56:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:56:

CATGACCACA GTGCACTTCA GTCTGTGYTG ACGCAGCCGC C                          41

(2) INFORMATION FOR SEQ ID NO:57:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:57:

CATGACCACA GTGCACTTCA GTCTGTCGTG ACGCAGCCGC C                          41

(2) INFORMATION FOR SEQ ID NO:58:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:58:

CATGACCACA GTGCACTTCA GTCTGTGCTG ACTCAGCCAC C                          41

(2) INFORMATION FOR SEQ ID NO:59:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO:59:

CATGACCACA GTGCACTTCA RTCTGCCCTG ACTCAGCCT                             39

(2) INFORMATION FOR SEQ ID NO:60:

(i) SEQUENCE CHARACTERISTICS:
            (A) LENGTH: 41 base pairs
            (B) TYPE: nucleic acid (C) STRANDEDNESS: single
            (D) TOPOLOGY: linear (xi) SEQUENCE DESCRIPTION: SEQ ID NO:60:

CATGACCACA GTGCACTTTC TTCTGAGCTG ACTCAGGACC C                41

(2) INFORMATION FOR SEQ ID NO:61:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:61:

CATGACCACA GTGCACTTTC CTATGAGCTG ACTCAGCCAC C                41

(2) INFORMATION FOR SEQ ID NO:62:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:62:

CATGACCACA GTGCACTTCA GRCTGTGGTG ACYCAGGAGC C                41

(2) INFORMATION FOR SEQ ID NO:63:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:63:

CATGACCACA GTGCACTTCW GCCTGTGCTG ACTCAGCCMC C                41

(2) INFORMATION FOR SEQ ID NO:64:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (xi) SEQUENCE DESCRIPTION: SEQ ID NO:64:

GAGTCATTCT CGACTTGCGG CCGCTGAACA TTCTGTAGGG GCCACTGTCT T        51

(2) INFORMATION FOR SEQ ID NO:65:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:65:

ATAAGCCCCG TAATCTCTTG C                                      21

(2) INFORMATION FOR SEQ ID NO:66:

(i) SEQUENCE CHARACTERISTICS:
            (A) LENGTH: 24 base pairs
            (B) TYPE: nucleic acid
            (C) STRANDEDNESS: single -continued

```
        (D) TOPOLOGY: linear (xi) SEQUENCE DESCRIPTION: SEQ ID NO:66:

GCBATGGTTG TTGTCATTGT CGGC                                            24

(2) INFORMATION FOR SEQ ID NO:67:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:67:

CAGGAAACAG CTATGAC                                                    17
```